United States Patent
Chen

(10) Patent No.: US 11,615,616 B2
(45) Date of Patent: Mar. 28, 2023

(54) USER-GUIDANCE SYSTEM BASED ON AUGMENTED-REALITY AND/OR POSTURE-DETECTION TECHNIQUES

(71) Applicant: Jeff Jian Chen, Braintree, MA (US)

(72) Inventor: Jeff Jian Chen, Braintree, MA (US)

( * ) Notice: Subject to any disclaimer, the term of this patent is extended or adjusted under 35 U.S.C. 154(b) by 116 days.

(21) Appl. No.: 16/837,485

(22) Filed: Apr. 1, 2020

(65) Prior Publication Data

US 2020/0311429 A1 Oct. 1, 2020

Related U.S. Application Data

(60) Provisional application No. 62/899,537, filed on Sep. 12, 2019, provisional application No. 62/876,832, (Continued)

(51) Int. Cl.
*G06V 20/20* (2022.01)
*A61B 5/11* (2006.01)
(Continued)

(52) U.S. Cl.
CPC ............ *G06V 20/20* (2022.01); *A61B 5/1116* (2013.01); *G06F 3/011* (2013.01); *G06F 3/167* (2013.01);
(Continued)

(58) Field of Classification Search
None
See application file for complete search history.

(56) References Cited

U.S. PATENT DOCUMENTS

| | | | |
|---|---|---|---|
| 2003/0021453 A1* | 1/2003 | Weise | H02K 3/24 382/128 |
| 2010/0319100 A1 | 12/2010 | Chen et al. | |
| 2012/0120113 A1* | 5/2012 | Hueso | G06F 3/011 345/672 |

(Continued)

FOREIGN PATENT DOCUMENTS

| CN | 107911621 A | 4/2018 |
|---|---|---|
| CN | 108491821 A | 9/2018 |

OTHER PUBLICATIONS

W-J. Wang, et al., Human Posture Recognition Based on Images Captured by the Kinect Sensor, 13 International Journal of Advanced Robotic Systems 10.5772/62163 (2016).

(Continued)

*Primary Examiner* — Steven Z Elbinger
(74) *Attorney, Agent, or Firm* — Modern Times Legal; Robert J. Sayre

(57) ABSTRACT

A user-guidance system that utilizes augmented-reality (AR) components and human-posture-detection techniques is presented. The user-guidance system can help users to use smart devices to conduct 3D body scans more efficiently and accurately. AR components are computer generated for the on-screen guidance to guide a camera operator to position the camera in a particular location in relation to a target object with a particular tilt orientation in relation to the target object to capture an image that includes a region of the target object for 3D reconstruction of the target object. Human-posture-detection techniques are used to detect a human user's real-time posture and provide real-time on-screen guidance feedback and instructions to the human user to adopt an intended best posture for 3D reconstruction of the human user.

20 Claims, 16 Drawing Sheets

Related U.S. Application Data filed on Jul. 22, 2019, provisional application No. 62/827,340, filed on Apr. 1, 2019.

(51) Int. Cl.
  *G06F 3/16*    (2006.01)
  *G06T 7/73*    (2017.01)
  *G06F 3/01*    (2006.01)
  *G06V 40/60*   (2022.01)

(52) U.S. Cl.
  CPC .............. *G06T 7/74* (2017.01); *G06V 40/67* (2022.01); *G06T 2207/30196* (2013.01)

(56) References Cited

U.S. PATENT DOCUMENTS

| | | | |
|---|---|---|---|
| 2014/0043328 A1* | 2/2014 | Chen | G06T 7/529 345/419 |
| 2014/0176565 A1 | 6/2014 | Adeyoola et al. | |
| 2015/0229838 A1 | 8/2015 | Hakim et al. | |
| 2017/0287212 A1 | 10/2017 | Tran | |
| 2018/0268565 A1 | 9/2018 | Dolin et al. | |
| 2019/0028637 A1* | 1/2019 | Kolesov | H04N 5/23293 |
| 2019/0282324 A1* | 9/2019 | Freeman | G09B 23/288 |

OTHER PUBLICATIONS

O. Khalifa, "Human Posture Recognition and Classification," 2013 IEEE International Conference on Computing Electrical and Electronic Enginneering (2013).

\* cited by examiner

USER-GUIDANCE SYSTEM BASED ON AUGMENTED-REALITY AND/OR POSTURE-DETECTION TECHNIQUES

RELATED APPLICATIONS

This application claims the benefit of U.S. Provisional Application No. 62/827,340, filed 1 Apr. 2019; of U.S. Provisional Application No. 62/876,832, filed 22 Jul. 2019; and of U.S. Provisional Application No. 62/899,537, filed 12 Sep. 2019, the entire contents of each of which is incorporated herein by reference.

BACKGROUND

The following discussion of the background state of the art may reflect hindsight gained from the disclosed invention(s); and these characterizations are not necessarily admitted to be prior art.

More and more sensors and displaying apparatuses have been integrated into smartphones and smartphone-like devices, including phones, iPads, tablets, or any similar type of device (i.e., having a display screen, a processor, and one or more of the sensors listed below) either mass-produced or customized for specific markets. For the purpose of this discussion, we generalize these devices as "smart devices". These sensors can include, for example:
  a. camera;
  b. camera array;
  c. depth sensors;
  d. GPS, location sensors;
  e. gyro sensors;
  f. acceleration sensors;
  g. orientation sensors;
  h. lasers;
  i. other types of sensors; and
  j. augmented-reality/virtual reality sensors.
These display apparatuses can include, for example:
  a. a generic smartphone display screen; and
  b. augmented reality/virtual reality specific displaying apparatus.

Among all of the above sensors, there is a category of sensor kit that combines all of these sensors and display-technologies to produce Augmented-reality (AR) and/or Virtual-reality (VR). These Augmented-reality-based (AR-based) and virtual-reality-based (VR-based) software packages, such as AR Core, AR Kit, VR kit, etc., are more and more available to consumer applications.

SUMMARY

Systems and methods for augmented-reality (AR) user guidance are described herein, where various embodiments of the system and methods may include some or all of the elements, features and steps described below.

The systems and methods described herein can provide the human user(s) with accurate yet simple user guidance instructions during a scanning process. The following discussion further illustrates the AR-based guidance techniques.

In a method of this disclosure, a three-dimensional model of a target object can be generated using a camera and a display screen with augmented-reality on-screen guidance. Augmented-reality components are computer generated to guide a camera operator to position the camera in a particular location in relation to the target object with a particular tilt orientation in relation to the target object to capture an image that includes a region of the target object. The computer-generated augmented reality components are displayed on the display screen where the camera operator can use the computer-generated augmented-reality components to position the camera in the particular location with the particular tilt orientation to then capture the image. The image from the camera is then received (e.g., in computer-readable memory in the camera).

Another method of this disclosure can be used in generating a three-dimensional model of at least one body part of a human using a camera and a display screen with human-posture-detection-based on-screen guidance. In this method, an image (taken by a camera operator) is received from a camera. The camera image includes at least one body part of the human to be modeled. The image of the at least one body part of the human is analyzed to identify the body posture of the at least one body part and the location and orientation of the at least one body part in the image received. On-screen guidance is provided on the display screen to guide positioning of the camera and positioning of the body part.

Also in accord with this disclosure, a computer-readable storage medium stores program code that, when executed on a computer system, performs a method for generating a three-dimensional model via the methods described herein.

BRIEF DESCRIPTION OF THE DRAWINGS

FIG. 21 is an illustration based on an actual picture of a room, while

FIGS. 24 and 25 show additional screen captures of the app taken during the scanning process using the exemplary 3D foot-shape scanning app, while

Figure 1:
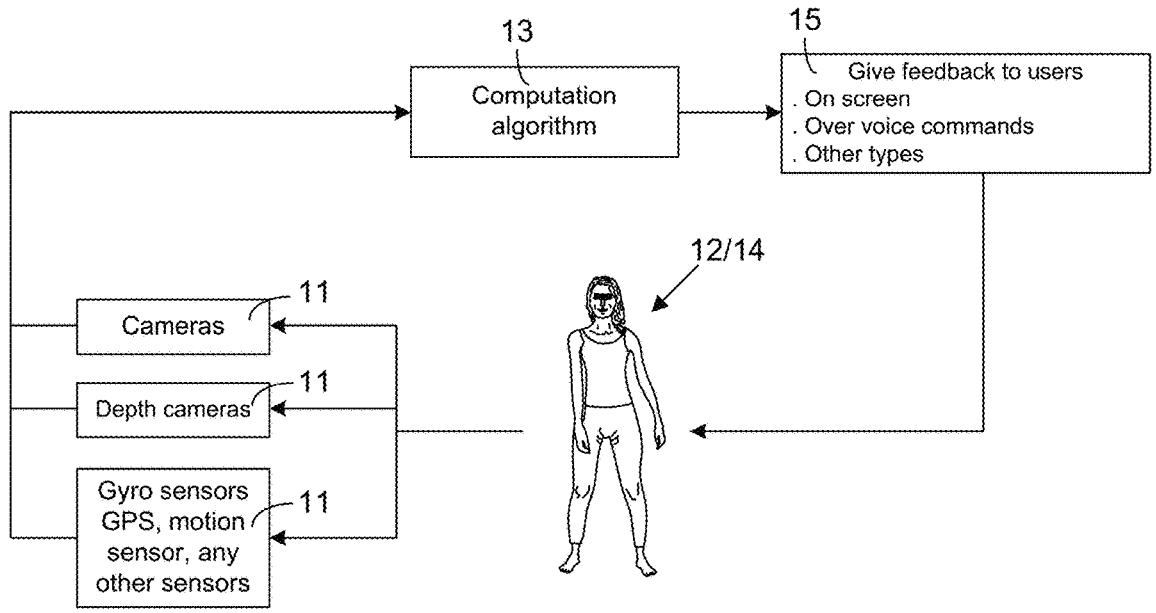
FIG. 1 schematically shows the flow of communications between components in an exemplary guidance system that instructs a scannee-person 14 or a scanner-person 12 to perform adjustments according to the feedback given by the exemplary guidance system.

In the accompanying drawings, like reference characters refer to the same or similar parts throughout the different views; and apostrophes are used to differentiate multiple instances of the same item or different embodiments of items sharing the same reference numeral. The drawings are not necessarily to scale; instead, an emphasis is placed upon illustrating particular principles in the exemplifications discussed below. For any drawings that include text (words, reference characters, and/or numbers), alternative versions of the drawings without the text are to be understood as being part of this disclosure; and formal replacement drawings without such text may be substituted therefor.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise herein defined, used or characterized, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular shape is referenced, the shape is intended to include imperfect variations from ideal shapes, e.g., due to manufacturing tolerances. Processes, procedures and phenomena described below can occur at ambient pressure (e.g., about 50-120 kPa—for example, about 90-110 kPa) and temperature (e.g., −20 to 50° C.—for example, about 10-35° C.) unless otherwise specified.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations and/or relative positions of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. The term, "about," can mean within ±10% of the value recited. In addition, where a range of values is provided, each subrange and each individual value between the upper and lower ends of the range is contemplated and therefore disclosed.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as those introduced with the articles, "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Smart devices (e.g., a smartphone) can be used to generate three-dimensional models (3D models) of a target object, for example, a human user. The smart device first acquires three-dimensional (3D) information of a human user using sensors attached to the smart device. This 3D information can include the background of the scene around the human user, 2D images of the human user, and other useful 3D information of the human user. The smart device can then upload this information to an external device or use the smart device's own computation power, itself, to reconstruct a 3D model of the human user. This entire process is referred to as a "3D scan" or a "3D scanning process", and the human user is referred to as a "user" in this disclosure from here on.

If the smart device is a smartphone, the 3D scan can be accomplished by a smartphone application (app) in the form of processor-executable software code stored in the memory of the smartphone.

Sometimes, the 3D scan needs to be performed by two users, where the first user holds the smart device to scan the second user. The first user is further distinguished as the scanner-person, and the second user is denoted as the scannee-person. Sometimes, the 3D scan can be conducted by a single user; hence, it is referred to as a self-scan, and the user is referred to as both the scanner-person and the scannee-person. A camera operator is defined as the user that operates the smart device (e.g., a smartphone with a camera) and conducts the 3D scan of the scannee-person. In the case of the two-user scan, the camera operator is the scanner-person, and in the case of a self-scan, the camera operator is the user him/herself (again both the scanner-person and the scannee-person). The smart device will collect scannee-person's 3D information to be used for constructing a 3D body model of the scannee-person.

A user-guidance system is usually needed during the 3D scanning process to help the user (i.e., the scannee-person and/or the scanner-person) collecting scannee-person's 3D information (e.g., pictures/video of the scannee-person). In the case where the smart device is a smartphone, this user-guidance system is usually part of the smartphone app. The user-guidance system in the smartphone app tells the scannee-person and/or the scanner-person what to do in the 3D scanning process in order to get the scannee-person body/body-parts 3D scanned—for example, where to stand in relation to the smartphone's camera position, how to strike the right poses in front of the smartphone camera, how to position the smartphone, how to tilt the smartphone to the right shooting angle, how long to hold one certain posture, etc.

In this disclosure, we present a user-guidance system that utilizes AR/VR techniques and/or human-posture-detection techniques, to read sensors' real-time data, compute sensors' data on-the-fly, and generate real-time guidance from the smart device to the user to guide the user step-by-step to perform the 3D scan. This user-guidance system can comprise on-screen guidance, voice guidance, haptic-feedback guidance, flash-light guidance, etc.

On a high-level, an exemplary user-guidance system includes the following parts, as shown in FIG. 1. In the 3D scanning process, the user-guidance system takes the output data of any or all of the sensors 11 (e.g., a camera, depth camera, gyro sensor, GPS sensor, motion sensor, etc.), analyzes the data and determines if the user(s) (either a scannee-person 14 or the scanner-person 12, or both) is performing the intended tasks (e.g., scanee-person having the right pose, standing at the right location in relation to the smartphone, the background being correct, etc.) via computation algorithms 13 stored on a computer-readable medium in communication with a computer processor that processes the algorithms (for example, on a smartphone). The processor then issues instructions to generate appropriate real-time feedback 15 communicated to the user via on-screen guidance, voice guidance, haptic guidance, etc., from the smart device. The user(s) then follows these prompts to adjust his/her pose; move himself/herself to the right location in relation to the smart device; move, tilt or rotate the smart device to the right location with the right camera angle; clean up the background environment; or move to a better background. The system functions as a feedback system that can generate and communicate, in real-time, clear instructions to the user 14 and/or user 12, so the user(s) can easily follow these instructions to comply with the requirements of the 3D scanning process.

Figure 2:
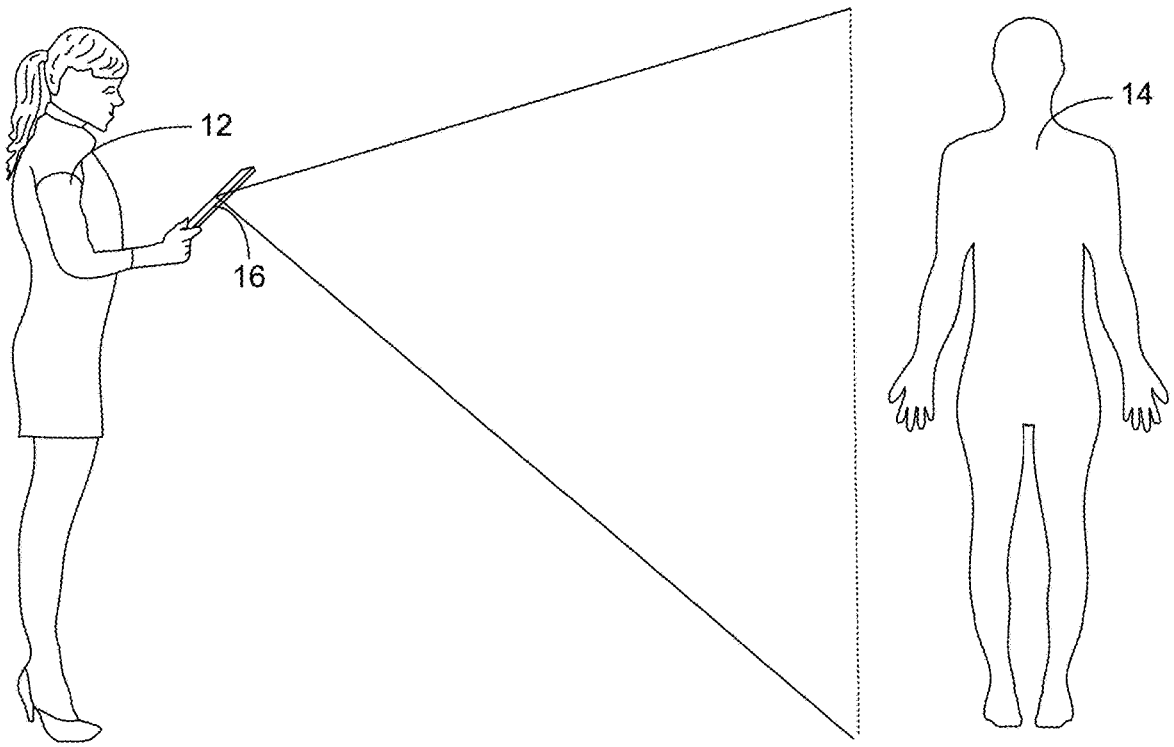
FIG. 2 shows a scanner-person 12 performing a 3D scan with a camera in an electronic device 16 on a scannee-person 14.
Figure 3:
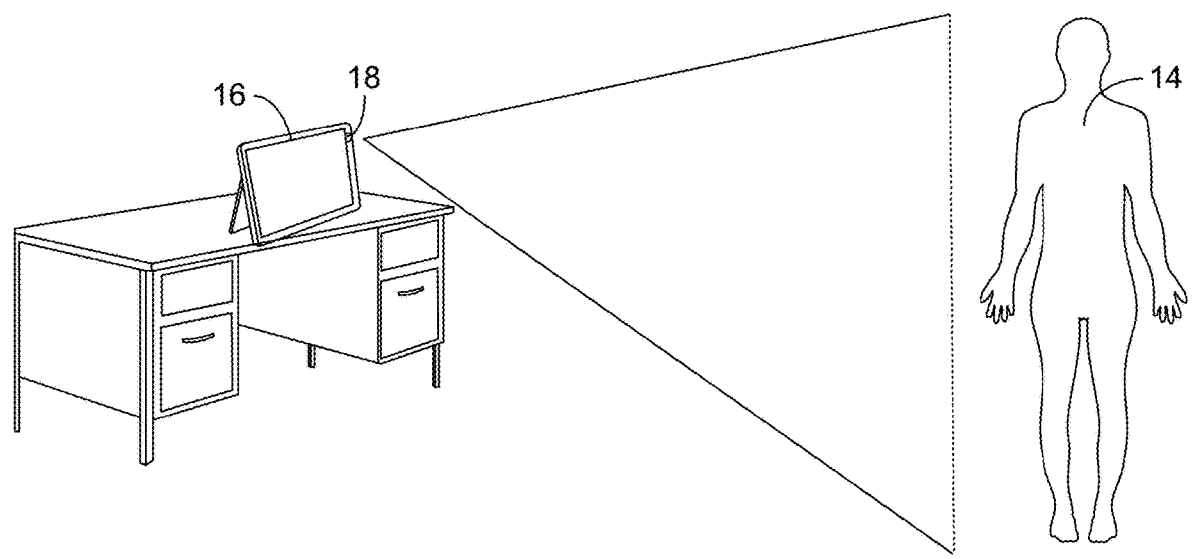
FIG. 3 shows a self-scan, where a scannee-person 14 scans himself by putting an electronic device 16, such as a smartphone, with a camera 18 in a stationary position and turns his body in front of the camera 18.

3D Scanning can be performed either by a scanner-person 12 operating a smart device 16 with a type of sensor (e.g., a smartphone with a camera or depth sensor or light-detection-and-ranging "LiDAR" sensor) to capture sensor data (e.g., images, videos, depth data, LiDAR data, etc.) of a scannee-person 14, as shown in FIG. 2 or by a scannee-person 14 performing a self-scan, as shown in FIG. 3. The sensor data can include a preliminary image to survey the scene before guidance components are generated, at least one image captured via guidance from guidance components, and additional images captured from the same or different perspectives to collect additional data. Other types of sensors, such as a depth sensor or a LiDAR sensor, can be used in other exemplifications to collect data that can assist in evaluating the position, shape, orientation, etc., of the target.

Example One

Figure 4:
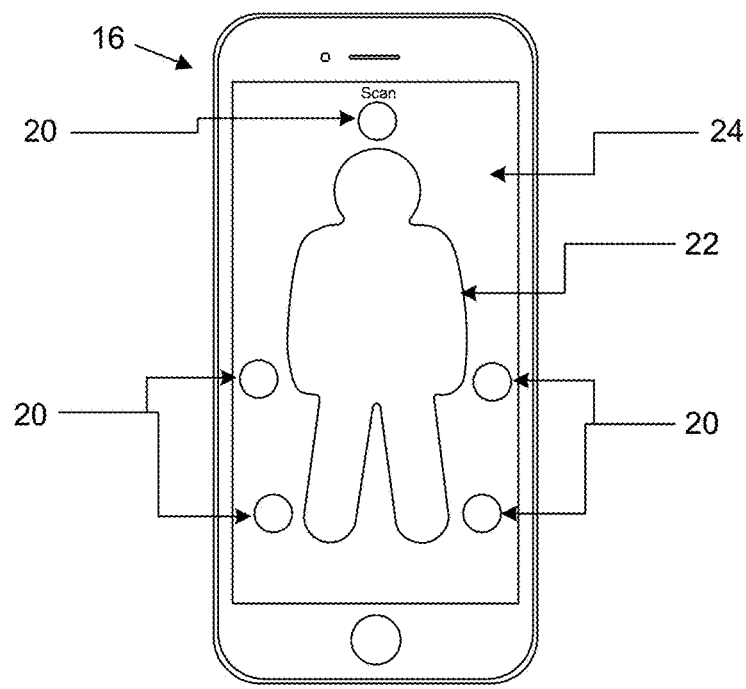
FIG. 4 shows a screen cap 24 of an app with multiple on-screen indicators 20 generated on the screen of a smartphone 16 and aligned with a representation of a human-shaped contour 22 to provide feedback as to whether a scannee-person 14 has achieved a desired pose.

A self-scan scenario is shown in FIG. 3, where a scannee-person 14 is using the front-facing camera 18 of a smartphone 16 and is facing the screen of the smartphone 16. The smartphone app first generates and communicates commands for producing a human-shaped contour on screen, as shown in FIG. 4, as on-screen guidance to visually instruct the scannee-person 14 how to pose in a particular stance in front of the smartphone camera 18. As can be seen, this stance is a simple standing pose with the scannee-person's feet shoulder-width apart and arms hanging to his/her sides. Voice guidance via voice prompt can also deliver this instruction to the scannee-person 14.

The user-guidance system then (a) uses an image/video stream captured by the camera 18 as the sensor input data in real-time, (b) rapidly processes the input data, (c) conducts image analysis, and (d) uses an algorithm to conduct real-time human-posture detection and extract the posture of the scannee-person 14 as well as his/her relative location from the smartphone. Note that, suitable techniques and algorithms using computer vision to determine the user's posture are described, e.g., in O. Khalifa, et al., "Human posture recognition and classification," International Conference on Computing, Electrical and Electronic Engineering 40-43 (2013); W. Wang, et al., "Human Posture Recognition Based on Images Captured by the Kinect Sensor," 13 International Journal of Advanced Robotic Systems 1-16 (2016); and T. Le, et al., "Human posture recognition using human skelton provided by Kinect," International Conference on Computing, Management and Telecommunications 340-45 (2013). The algorithm can detect where the scannee-person's hands, feet, head, etc., are located, all in real-time.

Based on the human-posture-detection result, the guidance system generates multiple on-screen guidance indicators 20, all in real time, to indicate whether or not the scannee-person's pose is in compliance with the requirements of the 3D scanning system. As shown in FIG. 4, as the five colored circles (with colors changing) next to the head, left hand, right hand, left foot, and right foot of the human-shaped contour are displayed on the screen of the smartphone 16 and serve as on-screen guidance indicators 20 of compliance. The colors of these circles 20 change into different colors to provide real-time feedback to the scannee-person as to whether or not she/he is properly adopting the intended pose and/or is at the intended distance from the camera and/or is standing in the intended spot of the room. Voice guidance can also be used in addition to the on-screen guidance. Accordingly, this interactive user-guidance system can help the scannee-person 14 to correct his/her pose in real-time.

Figure 5:
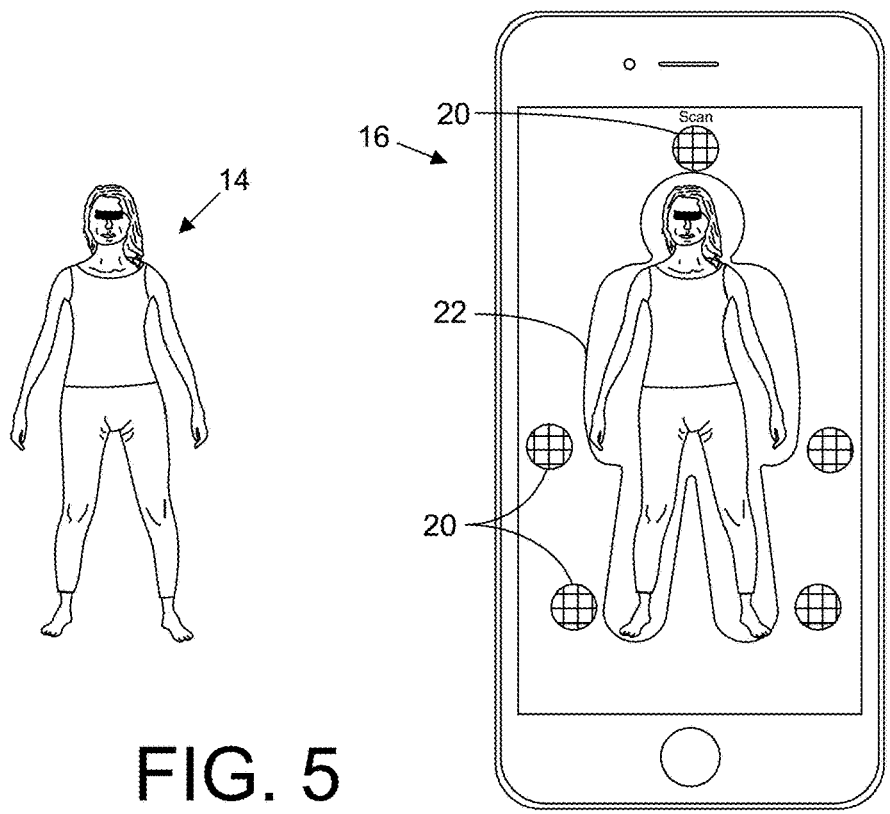
FIG. 5 shows the scannee-person 14 and the on-screen indicators 20 of FIG. 4, where the five body parts aligned with the indicators 20 are all in the desired positions and where the indicators 20 are colored (e.g., in green) to indicate that compliance.

As shown in FIG. 5, if each of the five parts of the scannee-person's body that are intended to be scanned is in its respective intended position, all of the colored circles 20 will be green.

Figure 6:
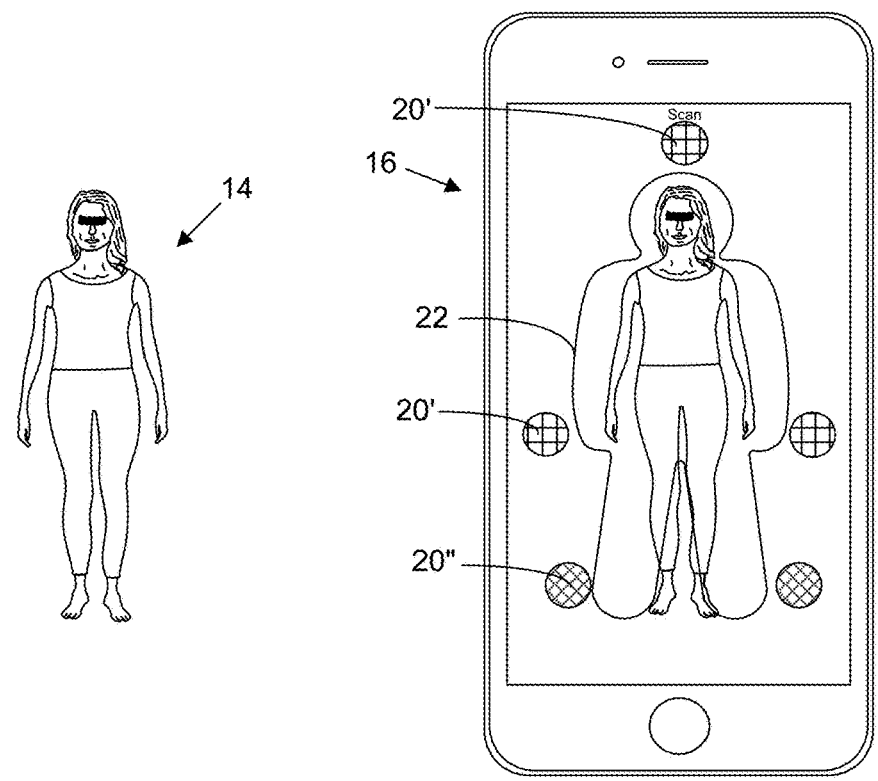
FIG. 6 shows the on-screen indicators 20 of FIGS. 4 and 5, where the feet of the scannee-person 14 are too close together, and where the indicators 20" proximate to the feet are a different color (red) from the indicators 20' for other body parts, which are properly positioned (with those indicators being green).

As shown in FIG. 6, if the scannee-person's two feet are too close according to the requirements, the circles 20 next to the feet are turned red, while the remaining circles 20 are green.

Figure 7:
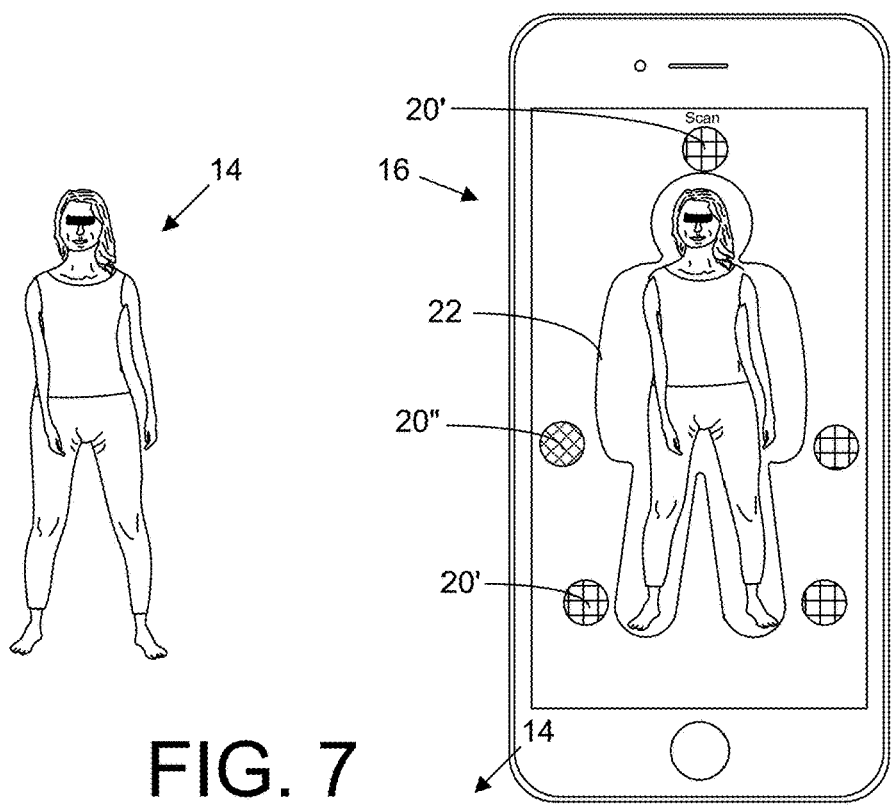
FIG. 7 shows the on-screen indicators 20 of FIGS. 4-6, where the right arm of the scannee person 14 is in the wrong position (as indicated by the coloring of the proximate indicator 20"), while the coloring of the other indicators 20' indicates that other body parts are in the desired position.

As shown in FIG. 7, in another scenario, if the feet and left arm of the scannee-person 14 are in the right positions and in the right pose but the scannee-person's right arm is not posing as required, only the circle 20 next to the right arm is turned red.

With this interactive real-time step-by-step on-screen guidance and voice guidance, based on the human-posture-detection results of the user, the user can easily complete the scanning process. The scannee-person's compliance in matching the specified poses is particularly important in the 3D scanning process, especially if there are any assumptions of the scannee-person's poses in the algorithm that reconstructs the scannee-person's 3D model in the down-stream process.

The above example only shows one of the scenarios, where the sensor input is the camera-produced image/video. Other types of sensor inputs can be utilized and processed to generate real-time on-screen guidance and voice guidance to guide the scannee-person to complete the image/video/user-data acquisition process for 3D-model reconstruction.

Furthermore, in a two-user scan scenario, where the scanner-person is holding the smartphone to conduct a 3D scan of the scannee-person, the scanner-person might also need to perform certain tasks following the real-time on-screen and voice guidance, for example, to adjust the distance between the smartphone and the scanee-person and/or to change camera shooting angle.

Lastly, the on-screen guidance and voice guidance can also be used to make sure that the background environment meets the requirements during the 3D scanning process.

Example Two

Figure 8:
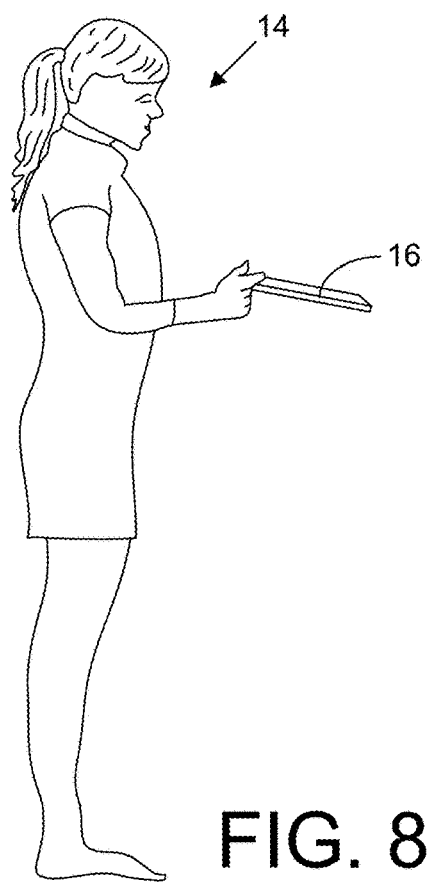
FIG. 8 shows another self-scan scenario where a scannee-person 14 is using the back-facing camera of a smartphone 16 to take 2D images of her foot to reconstruct her 3D foot model

Another self-scan scenario is shown in FIG. 8, where the scannee-person 14 is using the back-facing camera of the smartphone 16 to take 2D images and/or videos of his/her foot (feet) and conduct a foot 3D scan by him/herself while looking at the screen of the smartphone 16 during the 3D scanning process.

Figure 9:
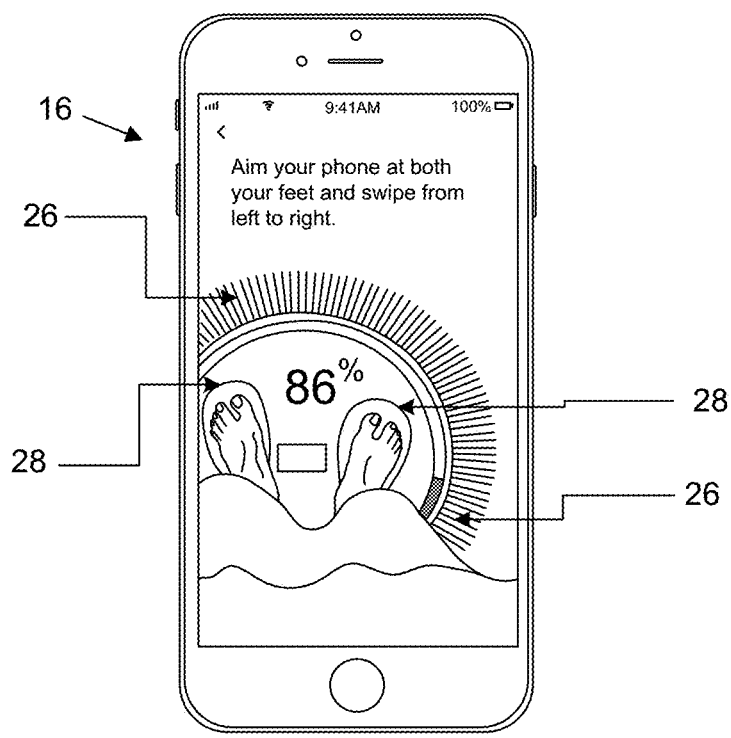
FIG. 9 shows the use of an AR floor mat 26 and augmented-reality foot contours 28 in the scanning of a scannee's feet.

The smartphone 16 will first survey the background environment around the scannee-person and generate an AR floor mat 26 at a certain location in the room, usually the center of the room or a spot where the background environment is less variable, as shown in the screen capture of the smartphone display shown in FIG. 9.

This AR floor mat 26 (and all other AR components described in this disclosure) does not exist in reality; rather, it is a computer-generated object that can only be observed in the viewing perspectives of the smartphone screen. Note, this is not just a paint-over picture affixed to a certain location of the display screen of the smartphone; rather, it is an AR component that exhibits its proper optical perspective and keeps its relative 3D position in relation to the rest of the real physical background when the smartphone changes its orientation and camera shooting angle.

Within the AR floor mat shown in FIG. 9, there is a pair of AR foot contours 28, also shown in FIG. 9. These AR foot contours 28 indicate to the scannee-person where his/her feet should be positioned during the foot 3D scanning process.

This on-screen guidance using the AR floor mat and AR foot contours will also be accompanied by voice guidance and/or additional on-screen indicators to provide clear instructions to the scannee-person, with which the scannee-person complies.

Figure 10:
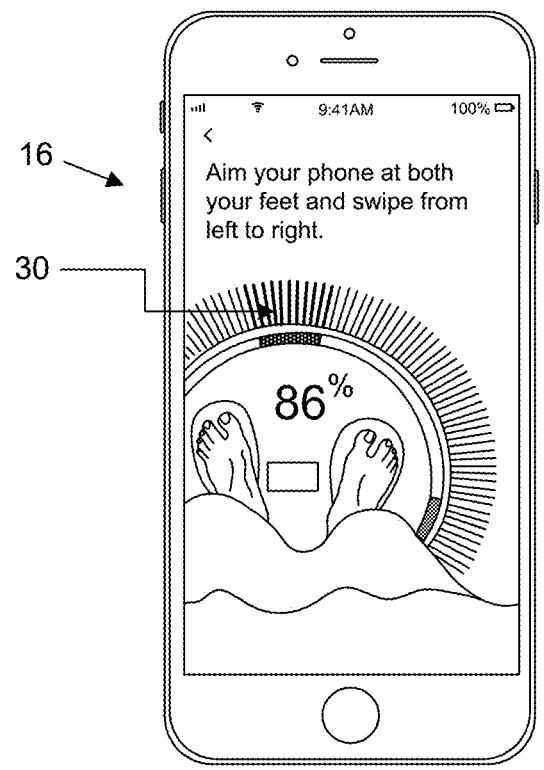
FIG. 10 shows the use of the AR floor mat 26 of FIG. 9, where a bad scanning section 28 that needs to be re-scanned.

For this particular example, after the scannee-person follows the instructions of the user-guidance system to stand on the two AR foot contours 28, he/she will perform a sweeping motion of his/her smartphone from the left side of his/her body to the right side of his/her body to take a video stream (or a series of picture snap-shots) of his/her feet from the left side of his/her body to the right side of his/her body. During this sweeping motion, the edges of the AR floor mat 26 can be turned into a progress bar, to indicate the progress (completeness) of the 3D scanning process. As shown in FIG. 10, for example, if the scannee-person misses one of the sections during the sweeping motion (e.g., by sweeping too fast in that section, perhaps) that section 30 of the progress bar's color becomes "red" and indicates to the scannee-person that the video stream taken from that particular section needs to be recaptured.

Example Three

In this example, we further present a complete step-by-step description of a user-guidance system employing AR techniques and using AR components as components of the real time user-guidance system to guide the user to complete the 3D scan in an efficient, interactive, and user-friendly way. This example is also a self-scan of the foot (feet), though the systems and methods can be applied to both self-scan and multiple-person-scan scenarios, as well as to a 3D scan of any body part.

Figure 11:
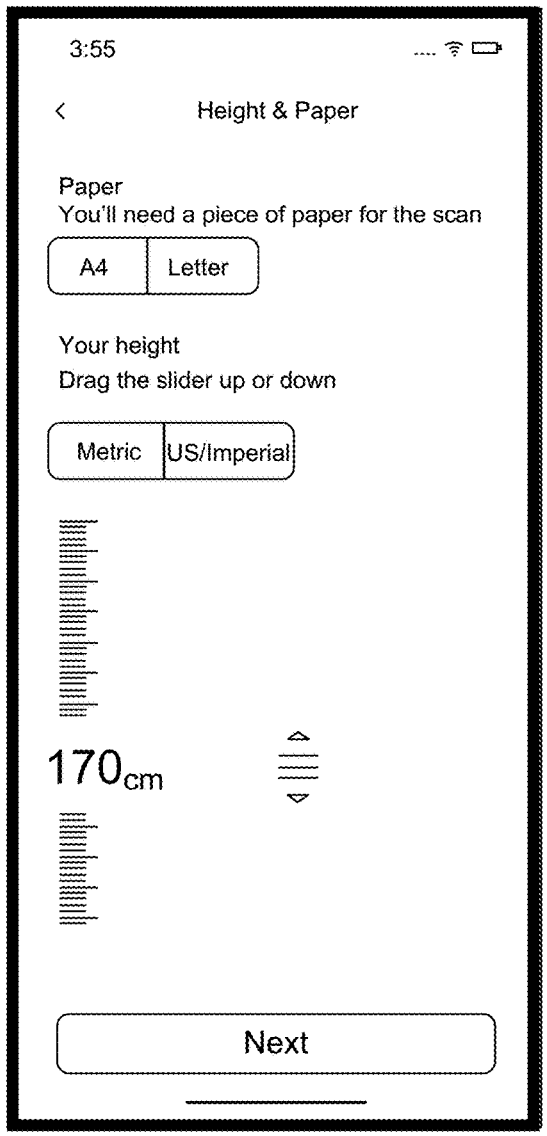
FIGS. 11 and 12 show screen captures of a display screen of a smartphone running an app requesting preliminary data to be used in performing the user-guidance methods described herein.
Figure 21:
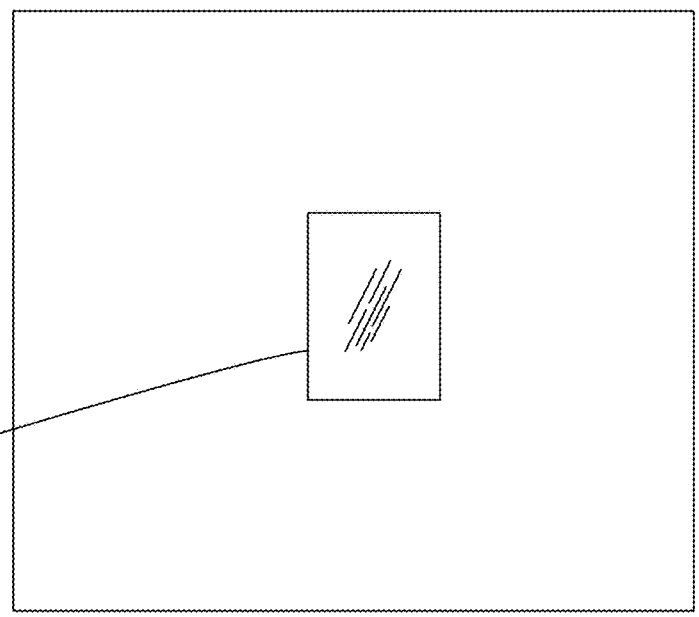

There are multiple Figures associated with this example, some Figures are illustrations of screen captures of the smartphone app when the user-guidance system is activated; some other Figures are illustrations based on photos of real-life scenes. In order for readers to differentiate these two different types of Figures, we are using the following conventions from here on: For screen captures of the smartphone app, screen captures in FIG. 11 onward have a thick black border, as shown in FIG. 11. Meanwhile, for pictures of real-life scenes, the Figures do not have a thick black border, as shown in FIG. 21.

A step-by-step illustration of how a user can use this smartphone app to conduct a self-scan of his/her feet, following the instructions from the user-guidance system, is provided, below.

Step 1: Information Intake

Figure 12:
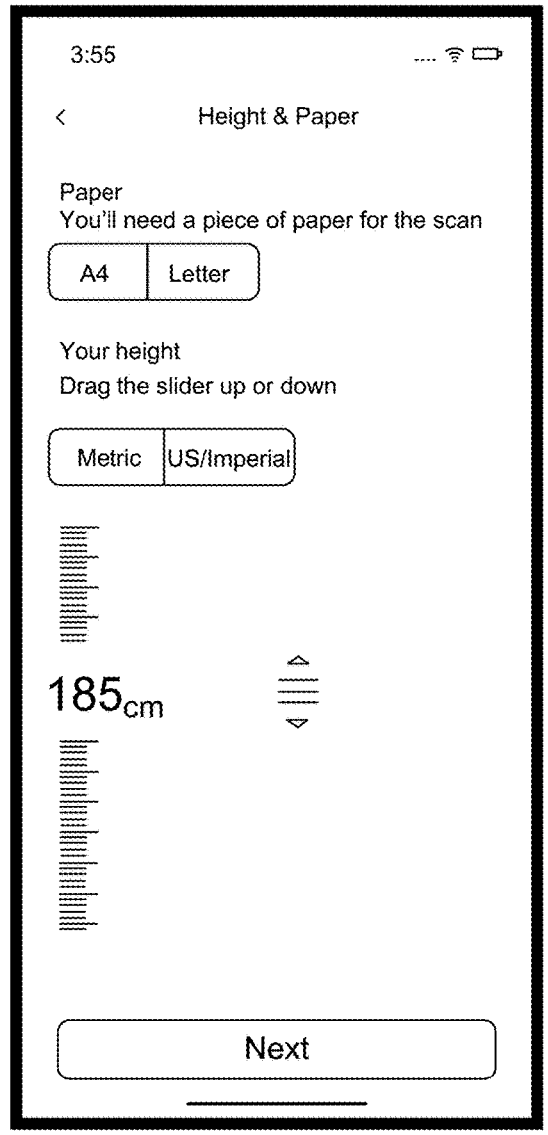

FIGS. 11 and 12 are screen captures of the exemplary 3D foot scanning app. At the commencement of execution of the app, the app generates on-screen prompts (e.g., printed text)

that ask the user a few questions to obtain some preliminary data. This data can be used to better construct the 3D models of the user's body/body parts (for this example, feet). These data can also be used to provide a better user experience.

In this exemplary app, it asks for the height of the user (either in a metric unit or in an imperial unit) and also asks what type of scaling reference object they are using (e.g., a sheet of either an A4 paper or a letter-sized paper).

Step 2: Specifications and Tutorial

Figure 15:
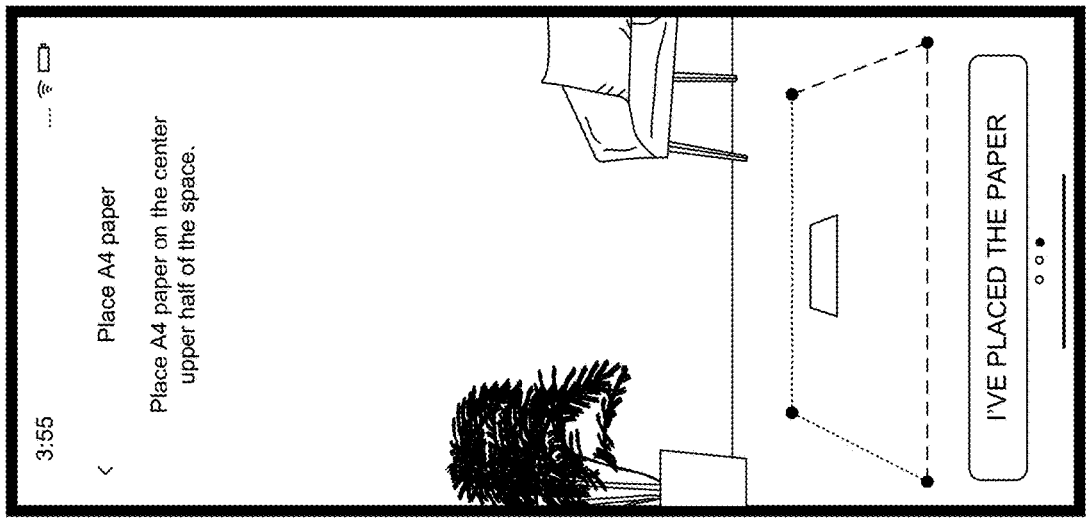
FIGS. 13, 14, and 15 show screen captures in the performance of an exemplary 3D foot-scanning process driven by an app that performs user-guidance methods described herein.
Figure 14:
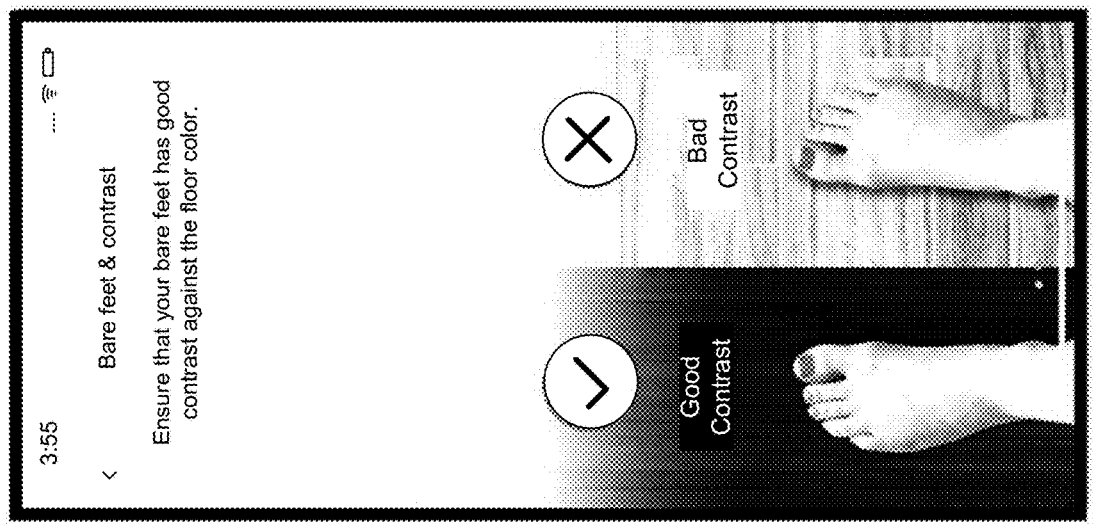
Figure 13:
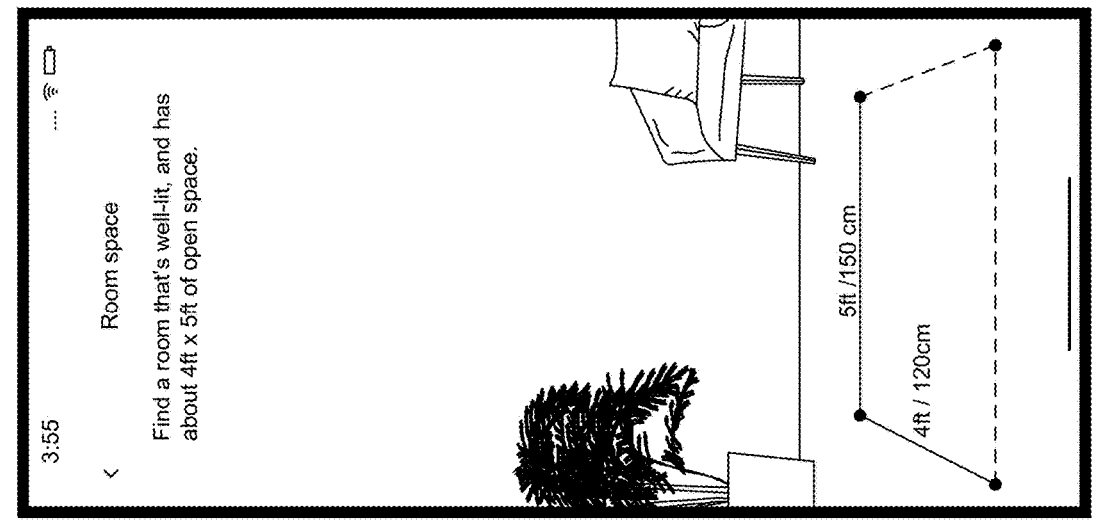

FIGS. 13-15 are the screen captures of the exemplary 3D foot-shape scanning app. After step 1 (information intake) is completed, the app generates a quick tutorial of the 3D scanning process as well as a few tips and requirements on the display. This tutorial of the 3D scanning process can be in a pictorial, video, audio, and/or text format. The tips/requirements step can also be interactive.

The screen captures presented in this step show only one example, which is in a pictorial format with texts explanations; but the systems and methods can be employed using any of a variety of other formats for communication with the user.

This exemplary app shows the user how big of an open space is needed for the 3D scan to take place (in FIG. 13); what type of floor-color shades are advantageous for the 3D scanning to be more accurate (in FIG. 14); and where to put the scaling reference object on the floor (in FIG. 15).

Step 3: AR Environment Setup

Figure 18:
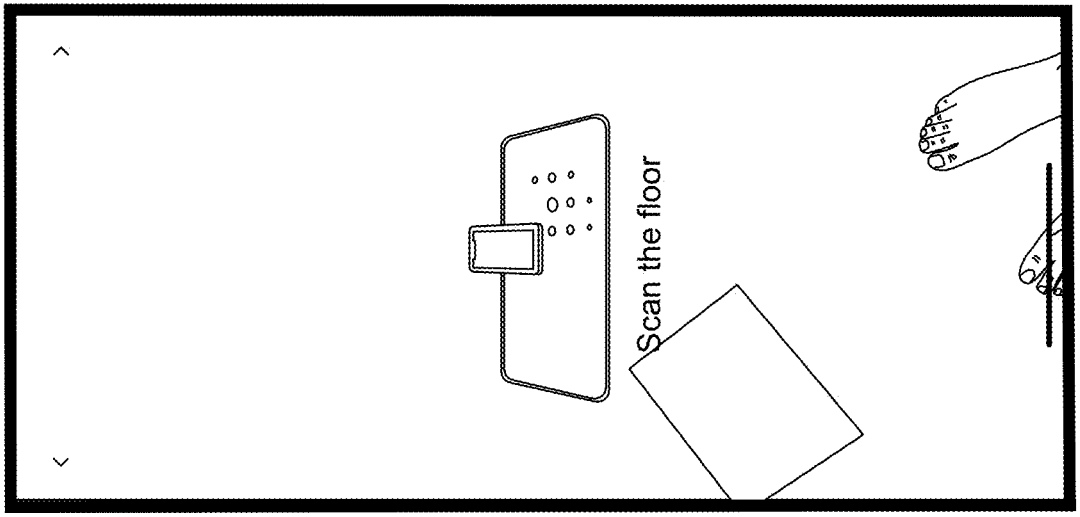
FIGS. 16-18 show additional screen captures of the app in the performance of the exemplary 3D foot-scanning process where the app provides instructions for the user to scan the floor.
Figure 17:
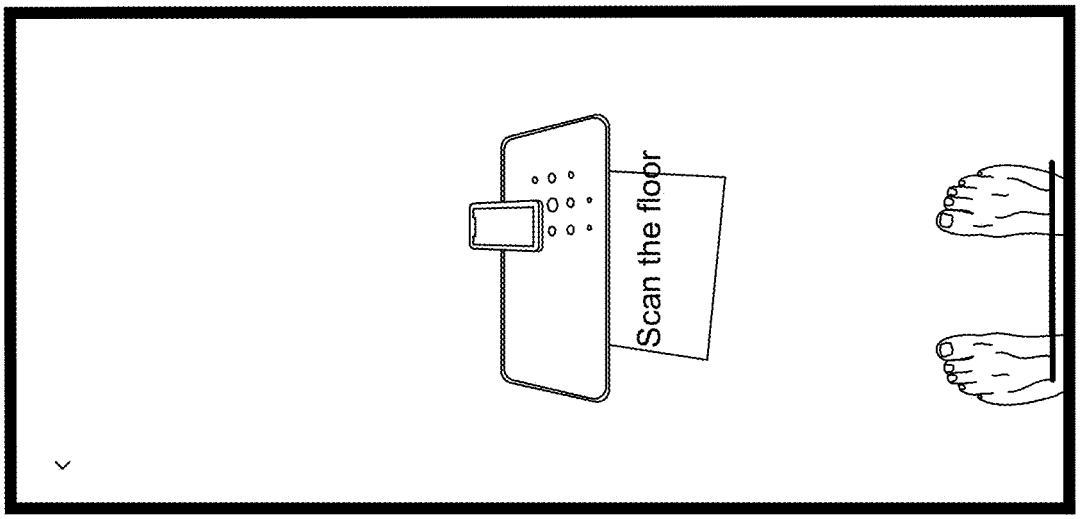
Figure 16:
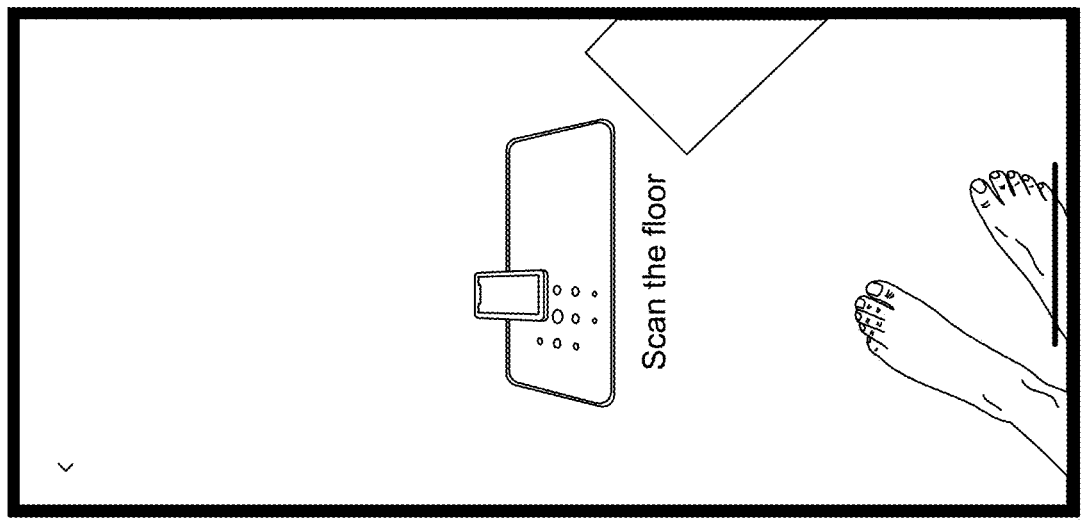

FIGS. 16-18 are screen captures of the exemplary 3D foot scanning app. After step 2 (specifications and tutorial) is completed, the user-guidance system asks the user to conduct an AR-environment setup; this setup can be carried out by the user performing a sweeping motion of the smartphone around the user's real environment. Of course, the user can also perform this AR-environment setup process by other means (e.g., via an automated displacement of a device incorporating a camera or via another human-generated motion), as the invention covers a more-general concept of setting up the AR environment as one of the steps in an AR-based user-guidance system; hence, this setup step is not limited to the sweeping motion only.

This exemplary app nevertheless generates indicators that ask the user to perform a sweeping motion to scan the floor, as shown in FIGS. 16-18, to complete the AR-environment setup.

Step 4: Scale/Location Reference Scanning

Figure 19:
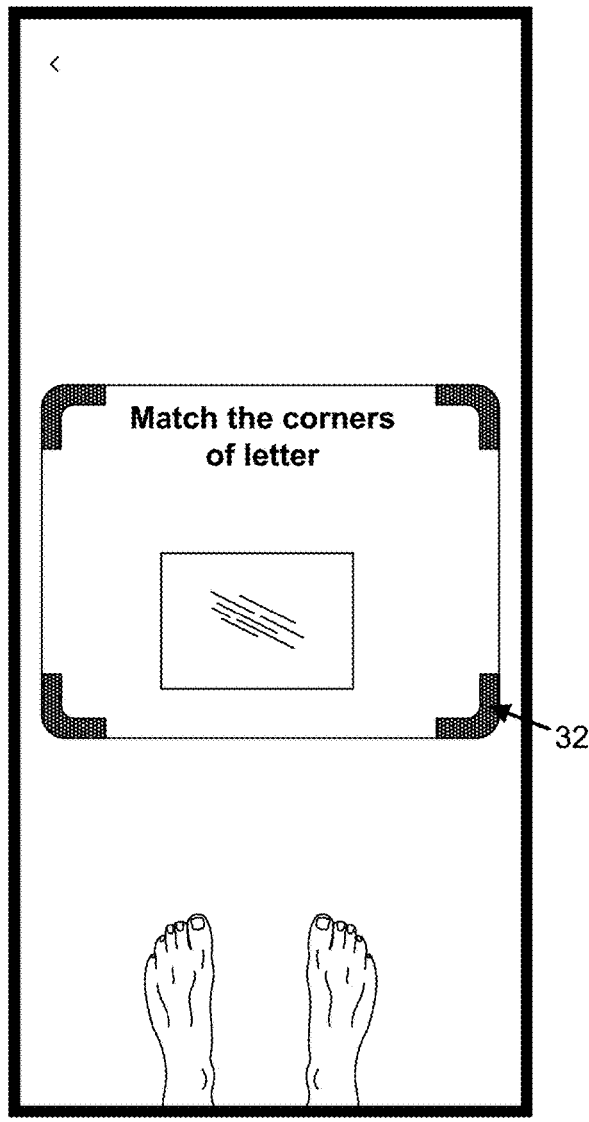
FIGS. 19 and 20 show additional screen captures of the app in the performance of the exemplary 3D foot-shaped scanning process where the app provides additional instructions 32 to the user for size and scale calibration.
Figure 20:
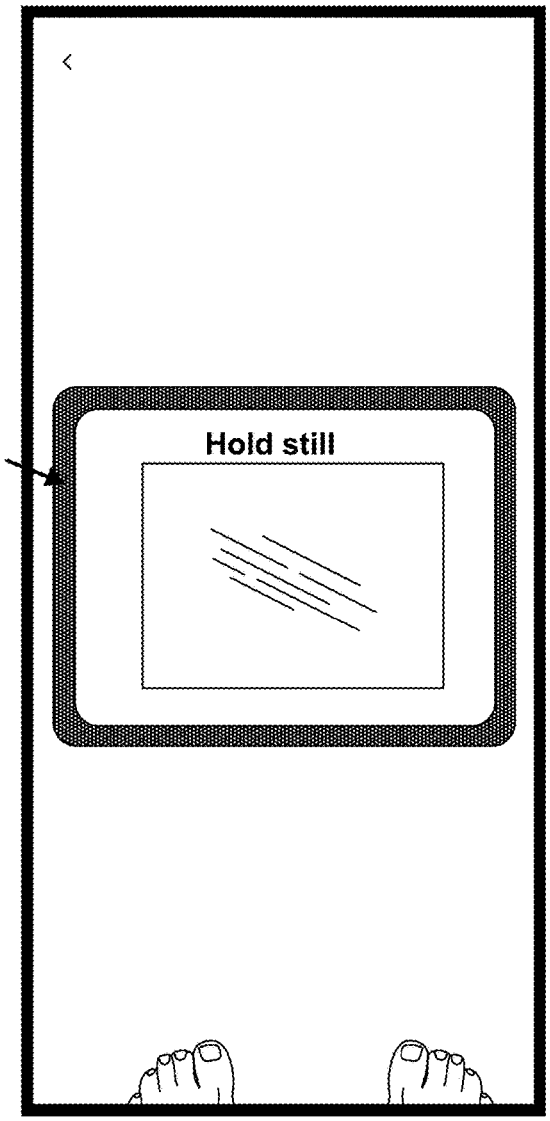

FIGS. 19 and 20 are the screen captures of the exemplary 3D foot scanning app while generating on-screen guidance 32 for scaling calibration. The app asks the user to perform a scaling calibration to obtain the actual size information of the environment, using a standard-sized object or shape as the reference object. In this exemplary app, the app uses an A4 or letter-sized paper. Note that there are other types of standard-sized reference objects that can be used for scaling calibration, such as credit cards, library cards, drivers' licenses, ID cards in general, coins, soda cans, smartphones themselves, etc. In general, the method can use a standard-sized object to calibrate for the scaling factor of the AR environment and/or scanning system and is not limited by the A4 or letter-sized paper.

Note that two or more standard-sized reference objects can be used together in this scaling calibration process, and that scenario is also included in the broader conception of the methods.

With this exemplary app, we show an example of the process, using a single standard-sized reference object to conduct scaling calibration of the AR system and/or the 3D scanning system. The app generates on-screen guidance indicators 32 that prompt the user to aim at the standard-sized reference object, as shown in FIG. 19, and hold the camera still, as shown in FIG. 20, to complete the task.

Step 5: AR Deployment

Figure 23:
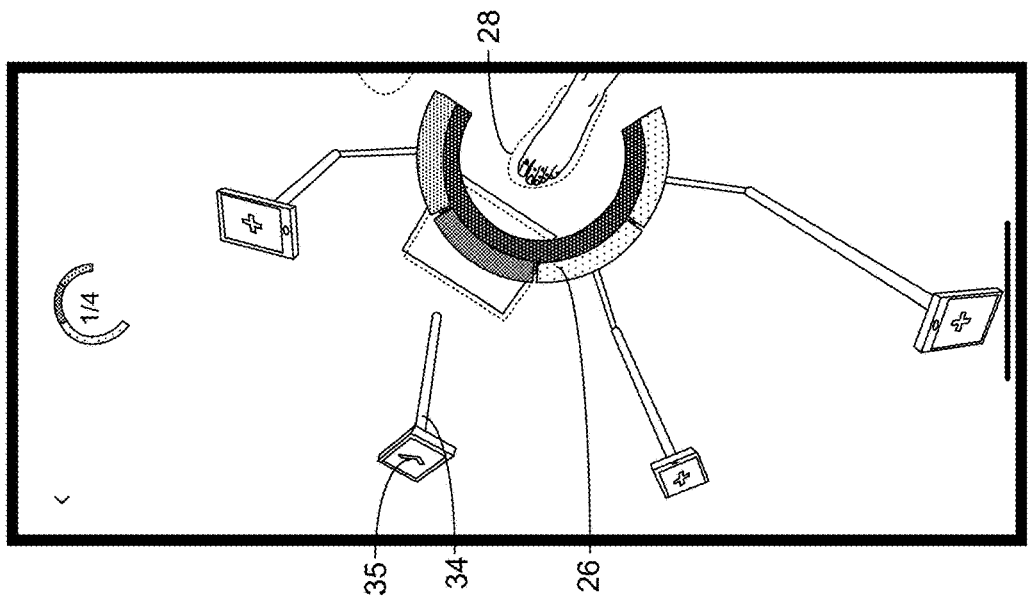
FIGS. 22 and 23 are screen captures of the app, shown with thicker borders and showing deployed AR components, including virtual pillars 34 for phone positioning and orientation as well as an AR floor mat 26 and AR foot contours 28, captured while camera images are being taken from different locations.
Figure 22:
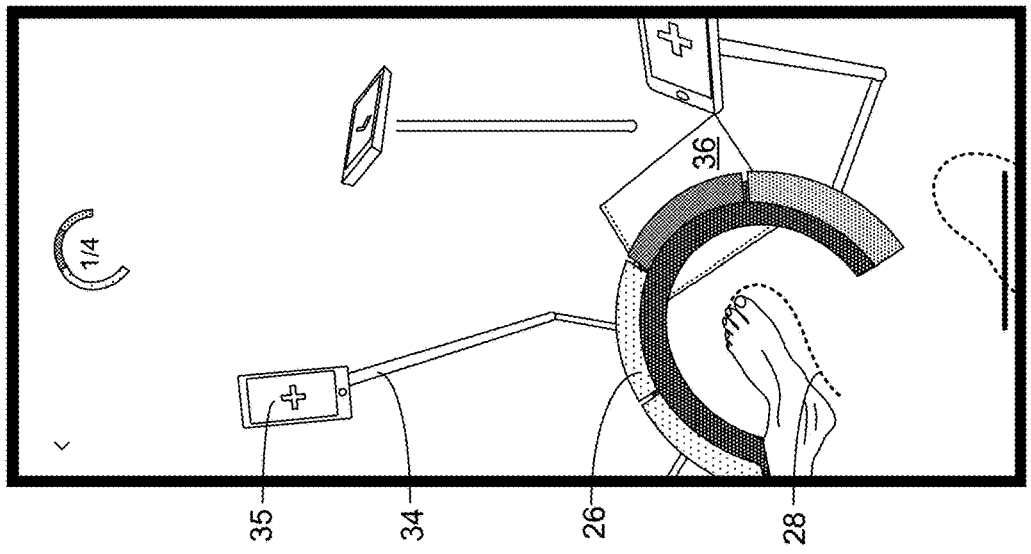

FIG. 21 is an illustration based on an actual real-life picture of the room where the 3D scanning is conducted, and FIGS. 22 and 23 are screen captures of the exemplary 3D foot scanning app. After step 4 (calibration), the app deploys AR components 26, 28 and 34 onto the on-screen guidance, as shown in FIGS. 22 and 23, together with other user-guidance components.

Motivations for implementing these AR components into the user-guidance system are described, as follows. Using the smartphone to perform accurate 3D body scanning is difficult, especially when it needs the user to take pictures/videos of the user's body/body parts at the right angles, from the right distances. In most cases, the accuracy of the 3D models generated from these pictures/videos hinges on the proper camera position and angle in relation to the scannee-person's body/body parts. Pictorial, voice, and/or text guidance can help; but, by incorporating AR components into the user-guidance system, it will be much easier for the user to understand exactly what needs to be done in the actual physical space to be compliant to the system requirements.

The AR components also convert what can be a somewhat boring process of 3D body scanning into a gamified, enjoyable experience, which provides the user with more motivation to take on the task.

FIG. 21 is an illustration based on a photo of the actual room where a user is conducting the 3D scan. As readers can see, the background is nothing but an empty floor with a piece of paper 36 (i.e., letter-sized paper as the standard-sized reference object) that was put there in step 4 by the user. Once the app completes the AR-environment setup and scaling calibration, the user-guidance system can deploy the AR components. FIG. 22 shows the AR components 26, 28, 34, and 35 that were deployed by the exemplary app. FIG. 23 shows the same set of deployed AR components 26, 28, 34, and 35 from a different viewing angle. As you can see, even though in reality there is only one piece of paper (serving as a reference object 36) on an otherwise empty floor—in the AR environment generated on the smartphone's display screen by the app, there are several computer-simulated objects (AR components) 26, 28, 34, and 35. These AR components exhibit proper optical perspective and keep their relative 3D positions in relation to the rest of the physical background environment when the smartphone changes viewing angle between FIG. 22 and FIG. 23. The AR components 26, 28, 34, and 35 will be used to guide the user in the next few steps to complete the 3D scan.

There are a few different types of AR components in this example, including the following:
- several virtual pillars 34 that extend from the surface of the real floor, with a virtual carton smartphone 35 at the top of each virtual pillar 34;
- a virtual floor mat 26; for this example, the virtual floor mat 26 is divided into four sections, where each section is facing a virtual pillar 34; and
- a pair of virtual footprints 28 that provide guidance to the user as to where to stand.

The detailed functionalities of each of these AR components 26, 28, and 34 will be elaborated in the next few steps.

Step 6: AR-Based Guidance—User Positioning

Figure 24:
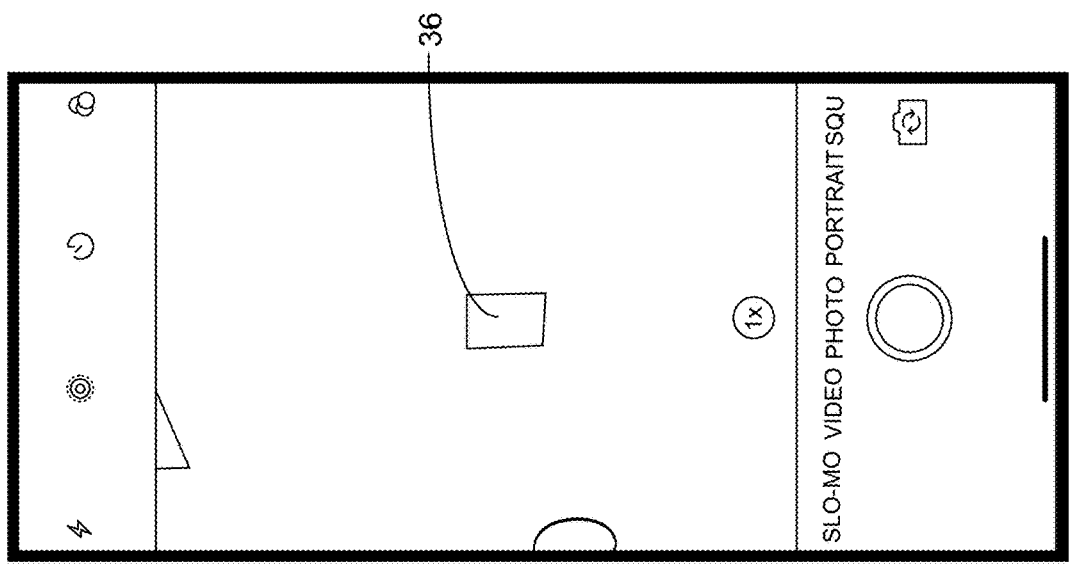
Figure 25:
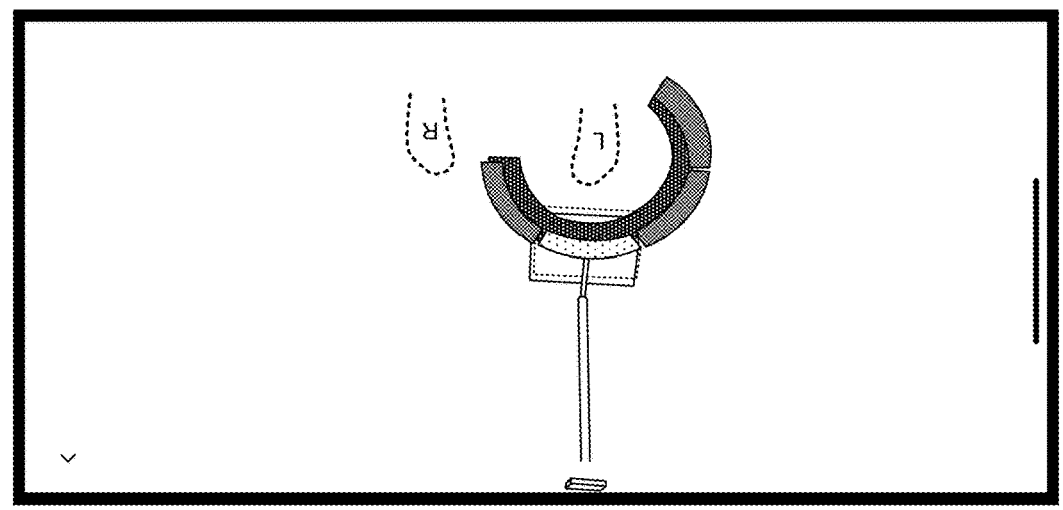

FIGS. 24 and 25 are screen captures of the exemplary 3D foot scanning app. The app's user-guidance system displays a few AR components 26, 28, and 34 on the app screen as on-screen guidance to guide the user to stand at the right place of the floor. Two out of the three AR components shown in FIGS. 24 and 25 are being used in this step: a virtual floor mat 26 and a pair of virtual footprint countours 28.

The app uses on-screen guidance and voice commands to guide the user to stand on the virtual footprint contours 28. The edge of the virtual floor mat 26 will serve as a progress indicator to the user as the user proceeds to conduct the 3D scan by taking multiple pictures of his/her foot from four different angles. The virtual floor mat 26 can also be used to display logos, advertisements, slogans, and other commercial usages on the screen via instructions provided by the app.

Figure 26:
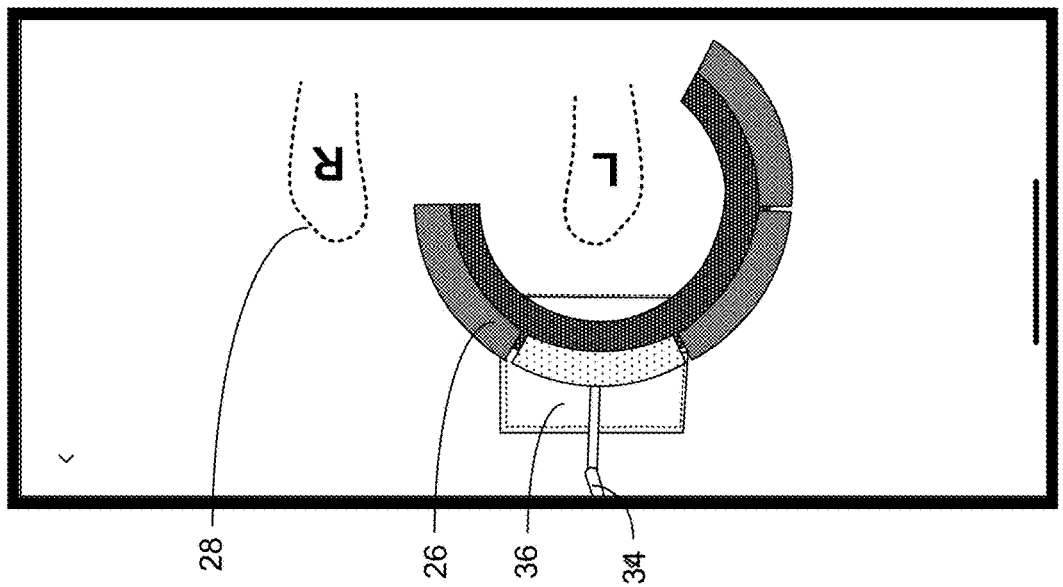
FIG. 26 is an illustration based a photo of an actual floor where scanning is to take place with a piece of paper used as a reference object 36.

An illustration based on a photo of the actual floor (in reality) is provided as FIG. 26; as we can see, it is simply an otherwise empty floor with a piece of paper (serving as a reference object 36) on it.

Step 7: AR-Based Guidance—Camera Distance and Shooting Angle

Figure 29:
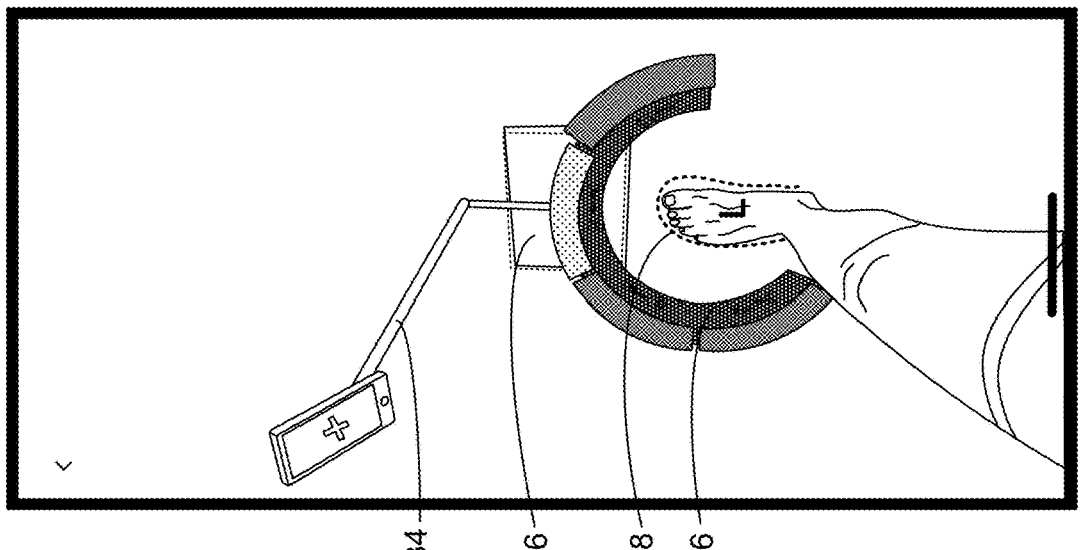
FIGS. 27, 28, and 29 show additional screen captures of the app taken during the scanning process using the exemplary 3D foot-shape scanning app, where a virtual pillar 34 extending from the floor is generated as an AR component of the image.
Figure 28:
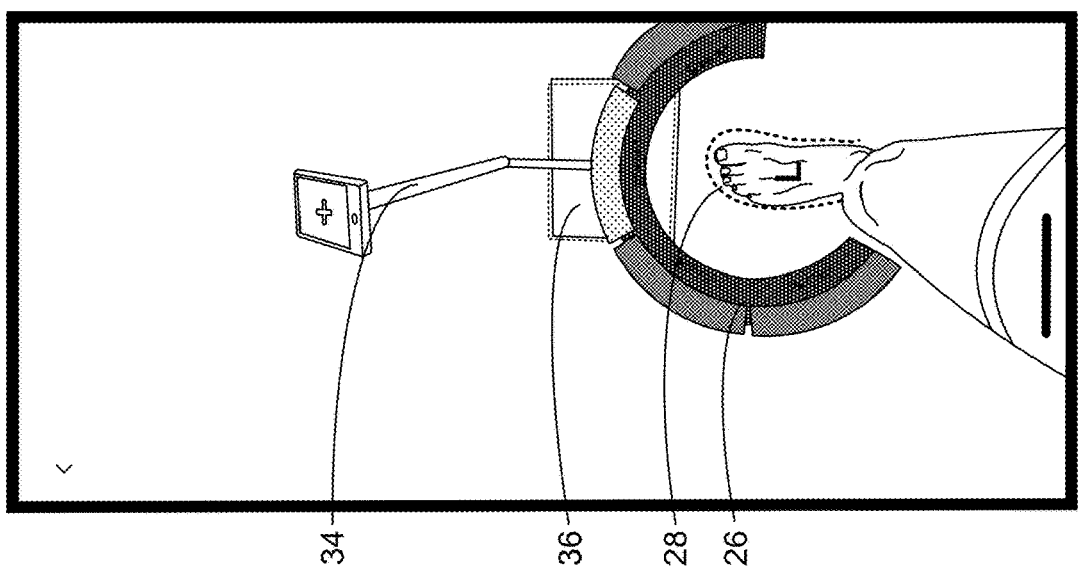
Figure 27:
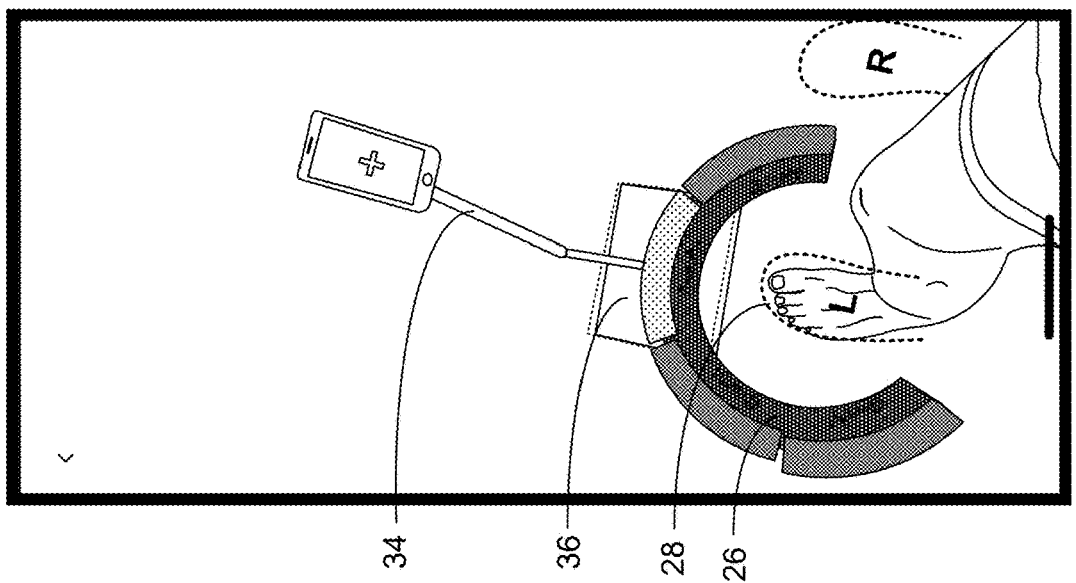

Additional screen captures of the exemplary 3D foot scanning app are provided as FIGS. 27-29. These screen captures show a virtual pillar 34 on the floor with a virtual smartphone 35 at the top of the virtual pillar 34. FIGS. 27-29 demonstrate three screen captures showing what the scannee-person sees on his/her smartphone display, when he/she moves the smartphone from the left of his/her left leg to the right of his/her left leg. One can see the characteristics and behavior of these AR components are very realistic.

Figure 32:
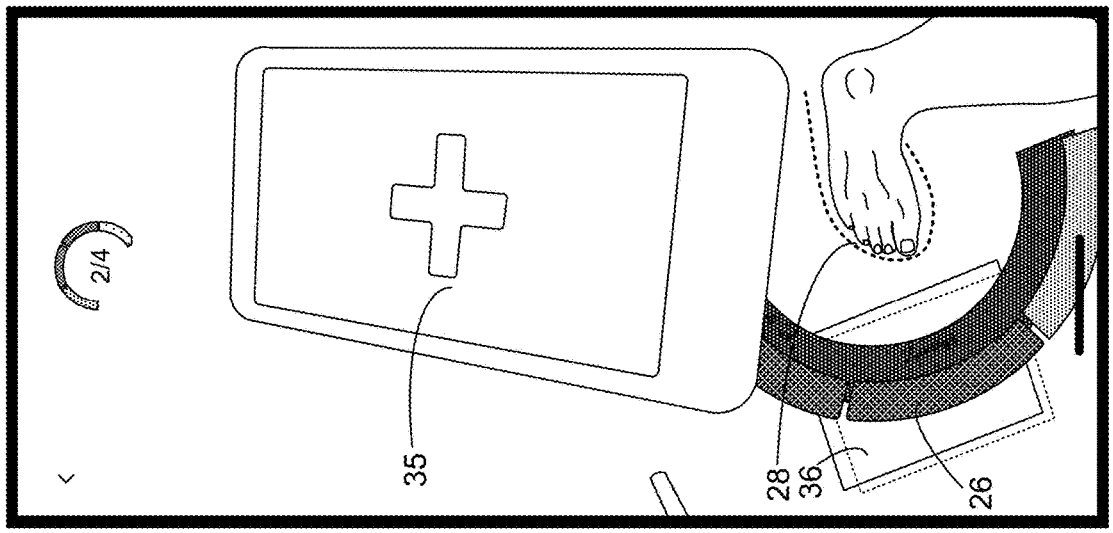
FIGS. 30, 31, and 32 show additional screen captures of the app taken during the scanning process using the exemplary 3D foot-shape scanning app, showing how AR components 26, 28, and 34 guide the user to complete the task of moving his/her real smartphone to a desired position.
Figure 31:
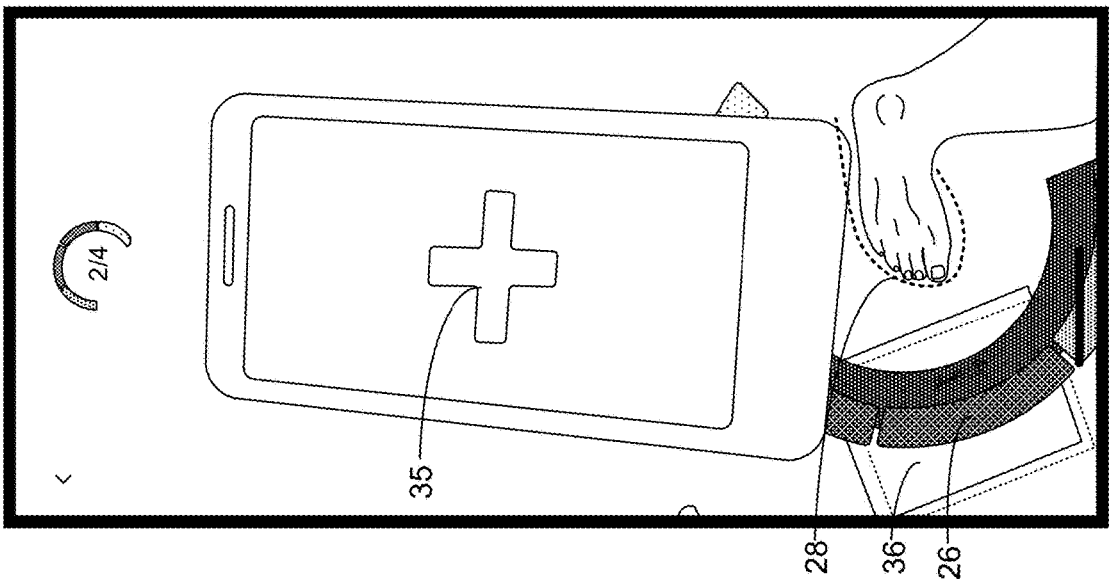
Figure 30:
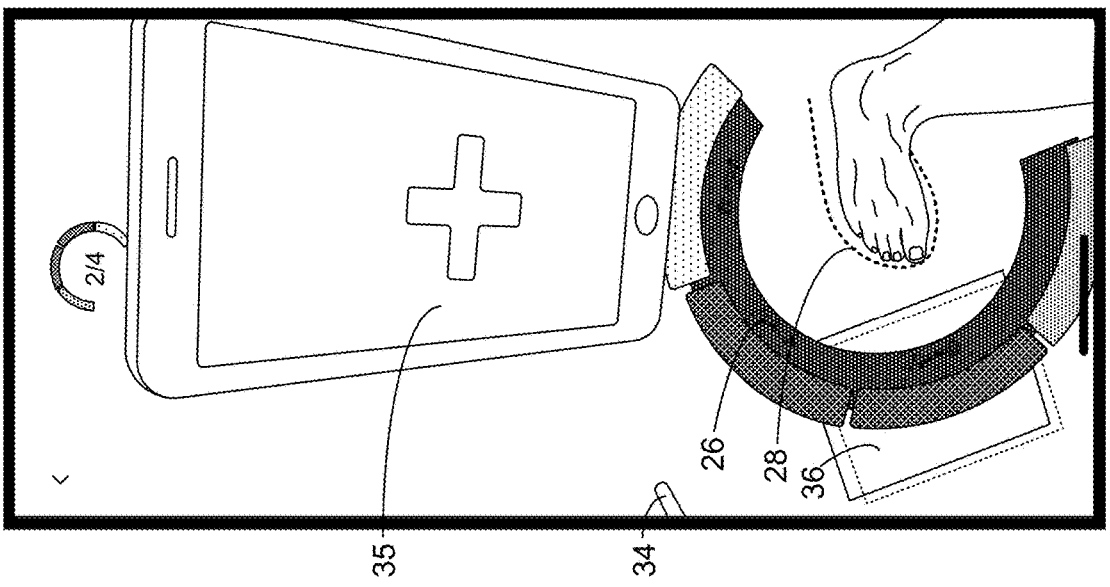

Another set of screen captures of the exemplary 3D foot scanning app are provided as FIGS. 30-32. These screen captures show how AR components 26, 28, 34, and 35 will guide the user to complete the task of moving his/her real smartphone (hence, the camera of his/her smartphone) to the specified position in reality.

When no user action is taken (i.e., the user keeps the smartphone motionless in real life), the virtual pillar 34 stays still while the virtual-carton smartphone 35 bobs up and down. The bobbing motion of the virtual-carton smartphone 35, together with the real-time voice guidance and text guidance from the app, instructs the user to move the smartphone in real life to the position of the virtual-carton smartphone 35. FIGS. 30-32 show the bobbing motion of the virtual-carton smartphone 35 when the screen captures are taken at different times while the user keeps the smartphone motionless in real life. One can see the bobbing motion of the virtual-carton smartphone 35 as the function of time.

Once the user follows the on-screen guidance and the voice guidance, and has moved the real smartphone to the position of the virtual-carton smartphone 35, the virtual pillar 34 and the virtual-carton smartphone 35 disappear to indicate that the user has completed this maneuver.

Note that if the user moves the smartphone away from this required position in real life, the disappeared virtual pillar 34 and virtual-carton smartphone 35 will re-appear to indicate that the user's smartphone's position is not meeting the user-guidance system's requirements anymore; and the user then needs to complete this step again.

Once the user completes this step, the x-y-z axial position of the user's smartphone camera in real life is fixed; In the next step, the user will follow the user-guidance system to tilt the smartphone camera at the specified angle, aiming at the foot of the user in real life, to conduct the image/video capture.

Screen captures of the exemplary 3D foot scanning app are provided as FIGS. 33-38. These screen captures show how AR components are used to guide a scannee-person 14 to complete the task of tilting his/her smartphone (hence, the camera of his/her smartphone) at the specified angle in real life. Note that the foot shown on the screen is an image of the real foot of the scannee-person 14 generated by the app using the video camera of the smartphone, not an AR component.

Figure 33:
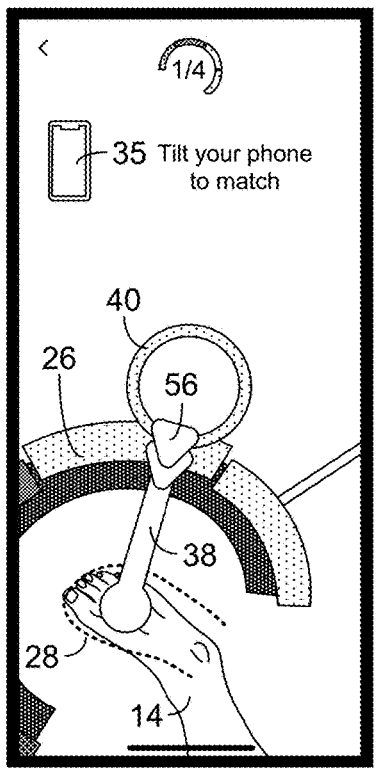
FIGS. 33-38 show additional screen captures of the app taken during the scanning process using the exemplary 3D foot-shape scanning app, showing how AR components 26, 28, 38, 40, 42, 44, 46, 48, and 50 guide the user to complete the task of tilting his/her smartphone to position it at a desired angle.
Figure 34:
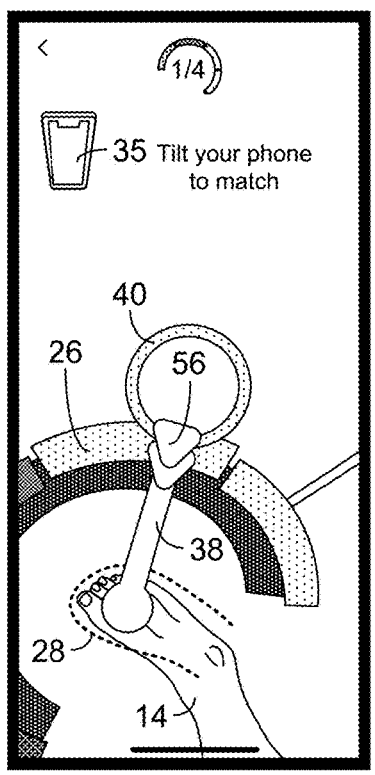
Figure 35:
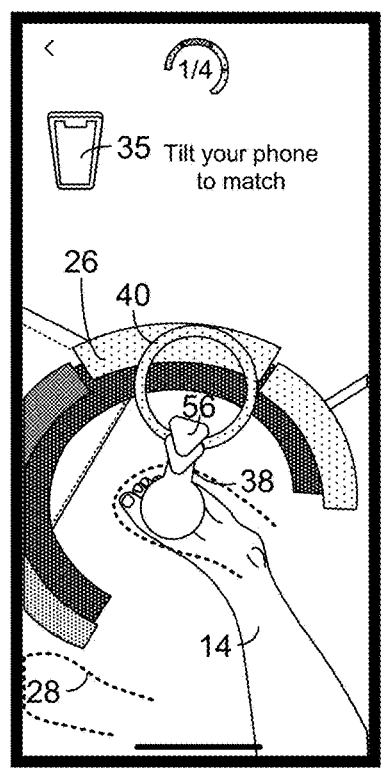

On the top part of the app screen in FIGS. 33-35, there is a virtual-carton smartphone 35 and a text message next to it. The tilt angle of the virtual-carton smartphone 35 mirrors the actual tilt angle of the user's real smartphone in real life. The text message generated by the app on the screen next to the virtual-carton smartphone 35 says "Tilt your phone to match".

As is also shown in FIGS. 33-35, the app generates, on the middle part of the screen, a grey virtual circular-ring structure 40, a white virtual double arrows 56 attached to the grey virtual circular-ring structure 40, and a red virtual-line segment with a rounded end 38, though choice in color or pattern usage for each component to distinguish different components from one another is arbitrary and non-limiting. The grey virtual circular-ring structure 40 indicated the spot on the floor at which the user's real smartphone camera is currently pointing; the white virtual double arrows 56 indicate the direction in which the user-guidance system instructs the user to change the pointing of the smartphone's camera in real life. The length of the red virtual-line segment with a rounded end 38 indicates the distance between the spot on the floor to which the user's real smartphone camera is currently pointing and the spot on the floor to which the user-guidance system instructs for the smartphone camera to point.

The rounded end in the red virtual-line segment 38 indicates the final desired pointing spot of the smartphone camera, which is the upper portion of the virtual footprint contour 28. As one can see, the on-screen guidance and the voice guidance instructs the scannee-person 14 to point his/her real smartphone camera at his/her foot.

The on-screen guidance uses its AR components and its non-AR components, such as an actual video stream and text, together with voice guidance to guide the scannee-person to complete the task of tilting his/her real smartphone (hence its camera) to the specified angle to aim at the virtual footprint contour 28 (hence at his/her right foot, since the user's foot is already positioned on the virtual footprint contours 28 from the previous step) so that the real smartphone camera can take a picture/video of the foot of the scannee-person 14 from the specified shooting angle.

The x-y-z position of the user's smartphone camera in real life is locked down in the previous step, and the tilt angle of the user's smartphone camera in real life is now locked down in this step. Hence, all degrees of freedom of the smartphone (hence the camera) are locked down by the user-guidance system.

FIGS. 33-35 show a series of screen captures taken when the user is gradually tilting his/her real smartphone from an initial tilt angle that is parallel to the floor (in FIG. 33) to a tilt angle that is about a 45-degree from the floor (in FIG. 35). During this process, the grey virtual-circular-ring structure 40 moves with the user's real smartphone's motion and gets closer and closer to the final desired pointing spot on the virtual footprint contour 28 (representing the real foot of the scannee-person 14); meanwhile, the red virtual-line segment 38 gets shorter and shorter.

Figure 36:
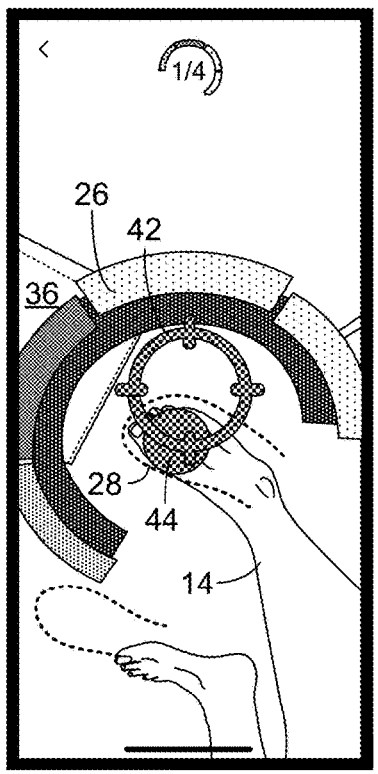

FIG. 36 shows that when the pointing of the real smartphone's camera is getting very close to the required pointing spot, the red virtual-line segment 38 is replaced by a beige circular target 44, and the grey virtual-circular-ring structure 40 is replaced by a beige rifle sight 42. This instantaneous AR components change is generated to further aid the user (scannee-person) to have finer control of his/her tilt motion so that the user can carefully tilt the smartphone camera in real life to point it to the spot represented by the beige circular target 44.

Figure 37:
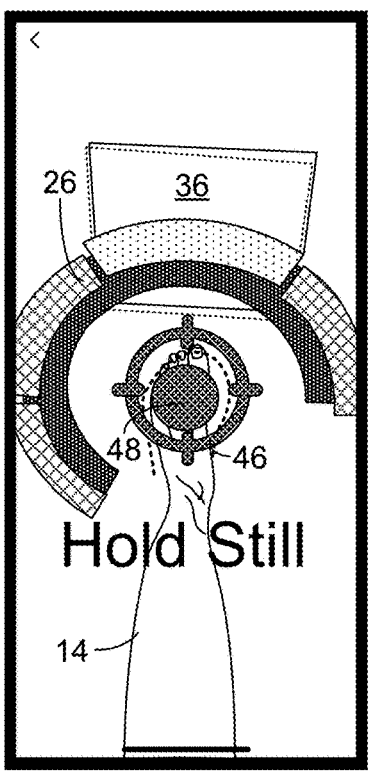

FIG. 37 shows that when the pointing of the user's real smartphone's camera is right on the required pointing spot, the color of the "beige circular target 44" and the "beige rifle sight 42" all become green (48 and 46); and large-font text, reading"Hold Still", is generated in the center of the screen. This generation of text happens when the user's smartphone camera is at the right x-y-z position and at the right tilt angle. This guidance message instructs the user to hold still, while the app is taking one or more pictures and/or videos of the user's foot. These pictures and/or videos will be used for 3D reconstruction of the user's foot.

Figure 38:
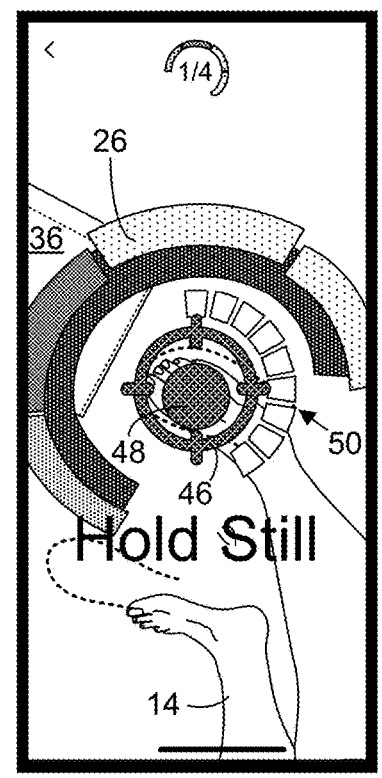

FIG. 38 shows that, when the app causes the picture/video to be taken, a progress bar 50 for the user is displayed.

This step 7 is repeated multiple times at different shooting angles around the scannee-person's foot to capture the picture(s)/video(s) of the his/her foot from different angles. An algorithm will be applied to reconstruct the 3D model of the user's foot based on these picture(s)/video(s). An example of a system that constructs the 3D model of a target object via its pictures is a computer-vision system. Two general references to computer-vision systems are "Computer Vision: A Modern Approach", by David A. Forsyth and Jean Ponce, Prentice Hall, 2002, and "Multiple View Geometry in Computer Vision", 2nd Edition", by Richard Hartley and Andrew Zisserman, Cambridge University Press, 2004.

A similar process is repeated for the scannee-person's other foot to complete the 3D reconstruction of both feet for the scannee-person.

The above three examples illustrate details of a novel user-guidance system that utilizes AR components and/or human-posture-detection techniques, and convey instructions to the users via on-screen guidance and voice guidance, to help the user to conduct a 3D scan. Some additional features that were not mentioned above can include the following:

Feature A: Task-Completion Indicators and Transitional Indicators

Figure 41:
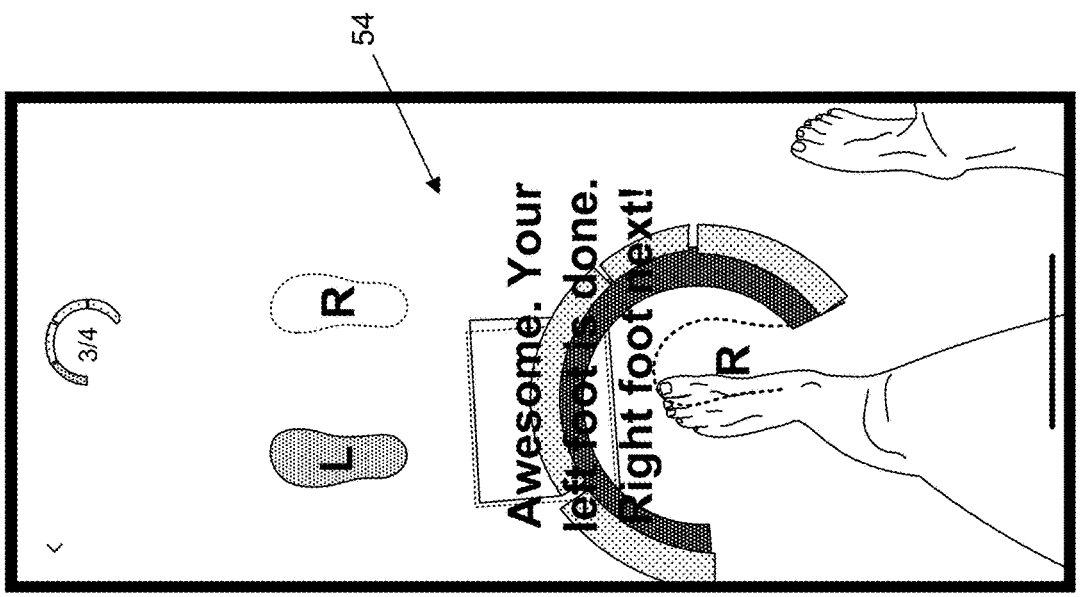
Figure 40:
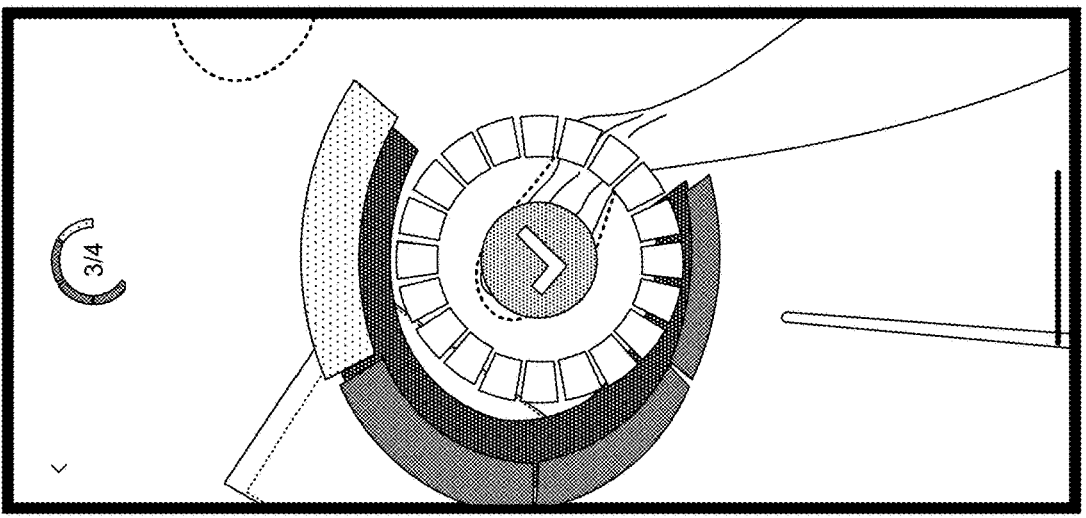
FIGS. 39 and 40 show screen captures of the app showing a few task-completion indicators, while FIG. 41 show a screen capture of transitional indicators.
Figure 39:
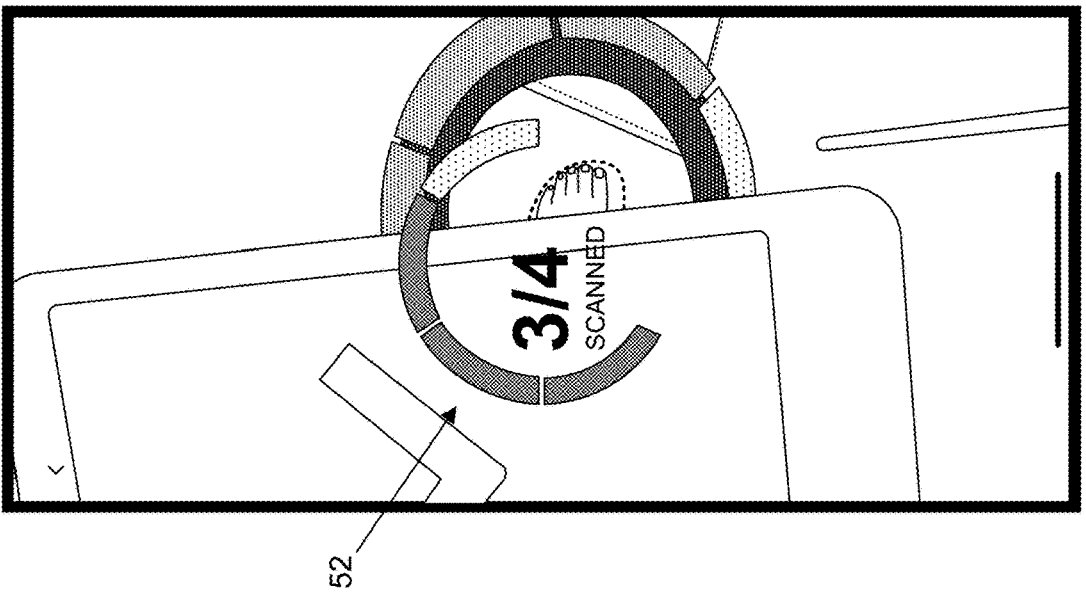

Screen captures of a few task-completion indicators are provided in FIGS. 39-41; they show screen captures of the task-transitional indicators both with and without the AR components. The AR component can be used as part of the task-completion indicator and the task-transitional indicator.

Feature B: Gradual Releases of Guidance Components

Figure 42:
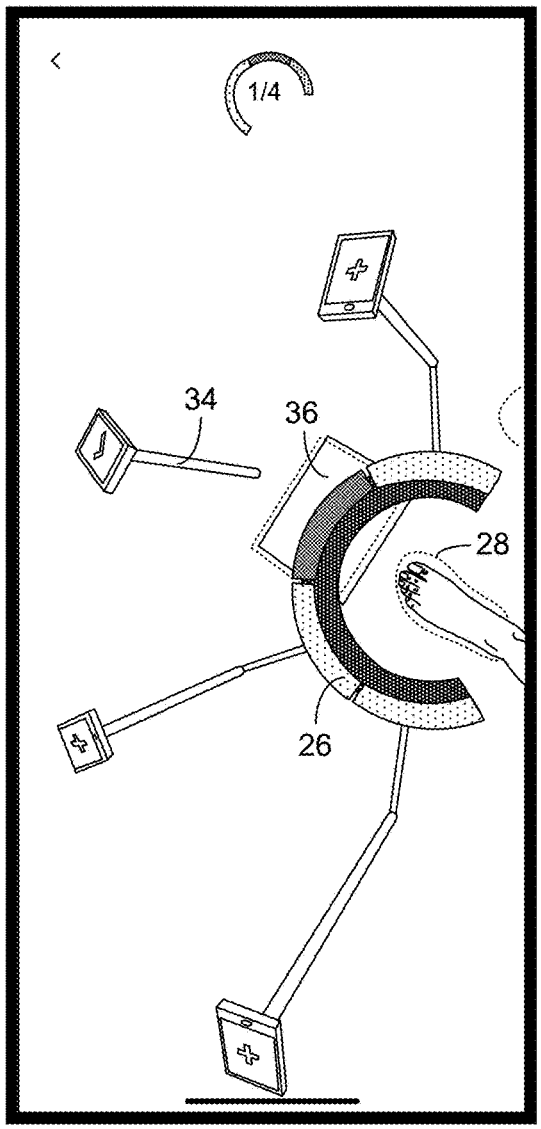
FIGS. 42 and 43 show screen captures of the app showing a scanning process using the exemplary 3D body-/foot scanning app, where AR components 26, 28, and 34 are turned on and off.
Figure 43:
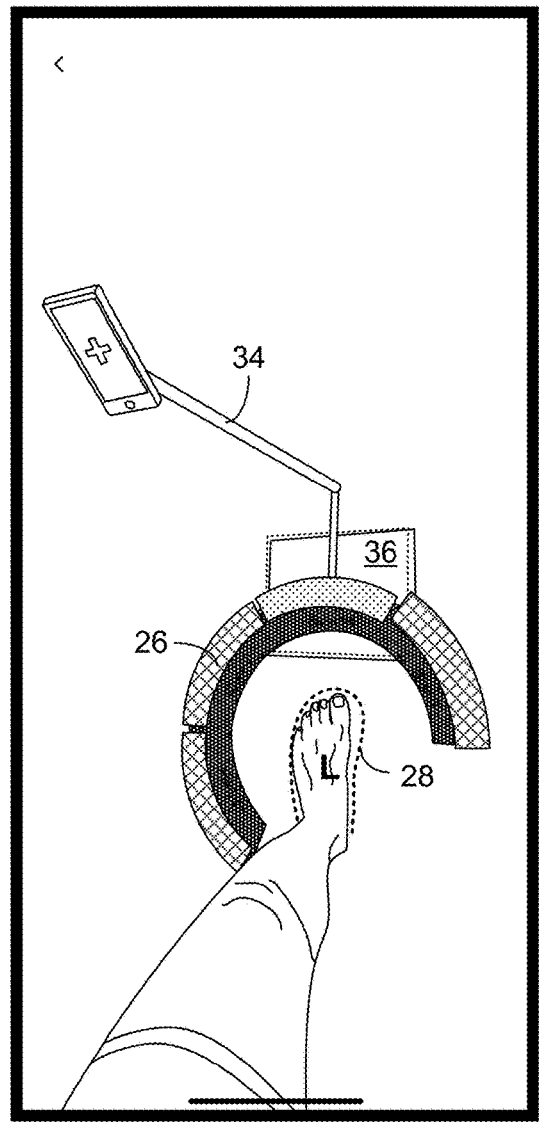

Screen captures of the exemplary 3D scanning app in example three are provided in FIGS. 42 and 43. These screen captures show that not all AR components need to be turned on simultaneously. Depending on the tasks the user-guidance system instructs the user to accomplish, it may be a good practice to turn on a specific set of the AR components during a certain task and turn off all other AR components; this way, the user can concentrate on the current task, and the unrelated AR components will not be a distraction to the user. FIG. 42 shows all of the virtual pillars 34 that the app will deploy during the entire process of the 3D scanning of the user's foot. FIG. 43 shows that, when providing alignment instruction to take the picture from a specific position and angle, the app only deploys one virtual pillar 34 for the specific position and shooting angle only so that the user can concentrate on that task at that moment, while all other virtual pillars 34 are hidden via the instructions generated by the app.

Feature C: Non-AR Components in the Guidance

In addition to the AR components of the user-guidance system, other sensor inputs and/or smartphone outputs can be used to generate instructions, as part of the user-guidance system. These sensor inputs can be from the smartphone's camera, GPS, wifi readouts, 4G signal readouts, gyro-sensor, magnetic sensor, geo-sensor, accelerometer, depth cameras, IR cameras, camera array, LiDAR sensor/scanner, etc. These smartphone outputs can include voice messages, images, sounds, text, camera flashlight, vibrations of the smartphone, or even a voice call from customer service directly to the smartphone to issue direct verbal guidance instructions to the user who is using the app to complete the tasks.

Feature D: Gamification of 3D Body Shape Scanning

The systems and methods described herein can make the 3D-scanning task fun and interactive for the user by implementing AR components and/or human-posture-detection techniques in the user-guidance system.

The app can take one more step of adding a reward system, where the user can be rewarded with points and benefits once he/she completes certain tasks during the 3D body-shape scanning process.

A reward system can also be employed to encourage the user to use his/her 3D body shape after the scanning is completed; for example, the app can reward the user with points or discount coupons when the user uses his/her body shape to shop for certain brands of clothing via the app's own e-commerce system.

Computer Implementation:

Though much of the above discussion is exemplified via a smartphone, which is a form of a computing device, running an app. The system and method can likewise be implemented/performed using any of a variety of computing devices that include or are in communication with a camera and an output device, such as a display screen.

In any case, the computing device operates as a system controller and can include a logic device, such as a microprocessor, microcontroller, programmable logic device or other suitable digital circuitry for executing the control algorithms; and the systems and methods of this disclosure can be implemented in a computing-system environment. Examples of well-known computing system environments and components thereof that may be suitable for use with the systems and methods include, but are not limited to, personal computers, hand-held or laptop devices, tablet devices, smart phones, multiprocessor systems, microprocessor-based systems, set top boxes, programmable consumer electronics, network PCs, minicomputers, distributed computing environments that include any of the above systems or devices, and the like. Typical computing system environments and their operations and components are described in many existing patents (e.g., U.S. Pat. No. 7,191,467, owned by Microsoft Corp.).

The methods may be carried out via non-transitory computer-executable instructions, such as program modules, e.g., in the form of an app. Generally, program modules include routines, programs, objects, components, data structures, and so forth, that perform particular tasks or that implement particular types of data. The methods may also be practiced in distributed computing environments where tasks are performed by remote processing devices that are linked through a communications network. In a distributed computing environment, program modules may be located in both local and remote computer storage media including memory storage devices.

The processes and functions described herein can be non-transitorially stored in the form of software instructions (e.g., as the app, described above) in the computing device. Components of the computing device may include, but are not limited to, a computer processor, a computer storage medium serving as memory, and a system bus that couples various system components including the memory to the computer processor. The system bus can be of any of several types of bus structures including a memory bus or memory controller, a peripheral bus, and a local bus using any of a variety of bus architectures.

The computing device can include one or more of a variety of computer-readable media accessible by the processor and including both volatile and nonvolatile media and removable and non-removable media. By way of example, computer-readable media can comprise computer-storage media and communication media.

The computer storage media can store the software and data in a non-transitory state and includes both volatile and nonvolatile, removable and non-removable media implemented in any method or technology for storage of software and data, such as computer-readable instructions, data structures, program modules or other data. Computer-storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can accessed and executed by the processor.

The memory includes computer-storage media in the form of volatile and/or nonvolatile memory, such as read only memory (ROM) and random access memory (RAM). A basic input/output system (BIOS), containing the basic routines that help to transfer information between elements within the computer, such as during start-up, is typically stored in the ROM. The RAM typically contains data and/or program modules that are immediately accessible to and/or presently being operated on by the processor.

The computing device may also include other removable/non-removable, volatile/nonvolatile computer-storage media, such as (a) a memory-card reader/write, (b) a hard disk drive that reads from or writes to non-removable, nonvolatile magnetic media; (c) a magnetic disk drive that reads from or writes to a removable, nonvolatile magnetic disk; and (d) an optical disk drive that reads from or writes to a removable, nonvolatile optical disk such as a CD ROM or other optical medium. The computer-storage medium can be coupled with the system bus by a communication interface, wherein the interface can include, e.g., electrically conductive wires and/or fiber-optic pathways for transmitting digital or optical signals between components. Other removable/non-removable, volatile/nonvolatile computer storage media that can be used in the exemplary operating environment include magnetic tape cassettes, flash memory cards, digital versatile disks, digital video tape, solid state RAM, solid state ROM, and the like.

The drives and their associated computer-storage media provide storage of computer-readable instructions, data structures, program modules and other data for the computer. For example, a hard disk drive inside or external to the computer can store an operating system, application programs, and program data.

The computing device can further include a network interface controller in communication with the processor and with an input/output device that communicates with external devices. The input/output device can include, e.g., input/output ports using electrically conductive wiring or wirelessly via, e.g, a wireless transmitter/receiver electrically connected with the system bus and in wireless communication with a wireless network router with which the external devices are also in communication.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step. Likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions, and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety for all purposes; and all appropriate combinations of embodiments, features, characterizations, and methods from these references and the present disclosure may be included in embodiments of this invention. Still further, the components and steps identified in the Background section are integral to this disclosure and can be used in conjunction with or substituted for components and steps described elsewhere in the disclosure within the scope of the invention. In method claims (or where methods are elsewhere recited), where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A method for use in generating a three-dimensional model of a target object using a camera and a display screen with augmented-reality on-screen guidance, comprising:

using augmented reality, computer generating and displaying augmented-reality components, including a virtual carton at a position on the display screen to guide a camera operator to align the camera with the position of the virtual carton on the display screen, wherein the position of the virtual carton corresponds to a particular location in relation to the target object at which the camera can capture an image that includes a target region of the target object;

adjusting at least one of the augmented-reality components to provide an indication on the display screen of a particular tilt orientation of the camera at which the camera can capture the image that includes the target region of the target object; and receiving the image from the camera after the camera operator uses the camera to capture the image with the camera aligned with the position of the virtual carton and having the tilt orientation indicated by the at least one augmented-reality component on the display screen.

2. The method of claim 1, further comprising generating a three-dimensional model of the target object from the received camera images.

3. The method of claim 1, further comprising:
using augmented reality, computer generating and displaying additional augmented-reality components, including the virtual carton at an updated position on the display screen to guide the camera operator to position the camera to align the camera with the updated position of the virtual carton on the display screen, wherein the updated position of the virtual carton corresponds to at least a second particular location in relation to the target object at which the camera capture an additional image that includes a second target region of the target object;
adjusting at least one of the augmented-reality components to provide an indication on the display screen of an updated tilt orientation of the camera at which the camera can capture the additional image that includes the second target region of the target object; and
receiving the additional image from the camera after the camera operator uses the camera to capture the image with the camera at the position corresponding to the updated position of the virtual carton and with the updated tilt orientation indicated by the at least one augmented-reality component on the display screen.

4. The method of claim 3, further comprising iteratively removing augmented reality components from the display screen or changing the appearance of augmented reality components as the camera operator completes the capturing of the image of one region of the target object and starts to capture the image of another region of the target object.

5. The method of claim 1, further comprising using at least one of sound, voice, haptic feedback, and flash-light as an additional part of the guidance to the camera operator.

6. The method of claim 1, wherein the target object includes at least one body part of an organism.

7. The method of claim 6, further comprising:
generating a three-dimensional model of the body part from the received camera images;
repeating the method of claim 3 at selected intervals over an extended period of time; and
comparing the three-dimensional models generated from camera images taken at different times to evaluate changes in fitness of the organism or growth of the organism over time.

8. The method of claim 6, wherein the organism is a human.

9. The method of claim 8, wherein the human is the camera operator.

10. The method of claim 9, further comprising presenting commands on screen to direct the human to move the at least one body part to an advantageous location and posture for image capturing.

11. The method of claim 8, further comprising fabricating wearable apparel sized and contoured to custom fit the at least one body part or selecting from pre-made apparel of different sizes to fit the at least one body part.

12. The method of claim 8, further comprising analyzing the images and identifying body parts of the human from the images.

13. The method of claim 8, further comprising using augmented reality to generate body part contours on the display screen to instruct the human where to position and orient the at least one body part.

14. The method of claim 1, wherein the camera and the display screen are incorporated into a smartphone.

15. The method of claim 14, further comprising generating the three-dimensional model of the target object from data from at least one sensor, wherein the sensor (a) is the camera and the data includes at least one camera image or (b) is selected from a depth sensor and a LiDAR sensor.

16. The method of claim 1, further comprising:
using augmented reality to generate a visual representation of a scaling reference object on screen to instruct the camera operator where to place the scaling reference object;
capturing at least one image of the scaling reference object after placement by the camera operator; and
determining dimensions of the target object using the information from the images of the scaling reference object and known dimensions of the scaling reference object or by providing on-screen instruction to the camera operator to position the camera at a fixed distance from the scaling reference object to provide definite size scale information.

17. The method of claim 1, further comprising
receiving a preliminary image from the camera, wherein the preliminary image is taken by the camera object and includes the target object; and
using the preliminary image to generate the augmented-reality components.

18. The method of claim 1, wherein the virtual carton has a shape of a smartphone and wherein the augmented-reality components further include a virtual pillar on which the virtual carton is mounted to indicate a height at which the camera is to be positioned.

19. A non-transitory computer-readable storage medium storing program code that, when executed on a computer system, performs a method for generating a three-dimensional model of a target object using a camera and a display screen with augmented-reality on-screen guidance, the method comprising:
generating instructions using computer generated augmented-reality components, including a virtual carton displayed at a position on the display screen to guide an operator of the camera to align the camera with the position of the virtual carton on the display screen, wherein the position of the virtual carton corresponds to a particular location in relation to the target object at which the camera can capture an image that includes a target region of the target object; and
generating instructions to adjust at least one of the augmented-reality components to provide an indication on the display screen of a particular tilt orientation of the camera at which the camera can capture the image that includes the target region of the target object.

20. The non-transitory computer-readable storage medium of claim 19, wherein the virtual carton has a shape of a smartphone and wherein the augmented-reality components further include a virtual pillar on which the virtual carton is mounted to indicate a height at which the camera is to be positioned.

* * * * *